(12) United States Patent
Henault et al.

(10) Patent No.: US 8,662,458 B2
(45) Date of Patent: Mar. 4, 2014

(54) INFUSION MANAGEMENT SYSTEM AND HOLDER

(75) Inventors: Mark Henault, Westminster, CO (US); James Kolozs, Denver, CO (US); Sean Cole, Denver, CO (US); Chad McKonly, Boulder, CO (US); Charles Cooper, Arvada, CO (US)

(73) Assignee: Firefly Medical, Inc., Fort Collins, CO (US)

( * ) Notice: Subject to any disclaimer, the term of this patent is extended or adjusted under 35 U.S.C. 154(b) by 28 days.

(21) Appl. No.: 13/021,025

(22) Filed: Feb. 4, 2011

(65) Prior Publication Data

US 2011/0290979 A1    Dec. 1, 2011

Related U.S. Application Data

(60) Provisional application No. 61/301,843, filed on Feb. 5, 2010.

(51) Int. Cl.
*A47K 1/04* (2006.01)
(52) U.S. Cl.
USPC ........ 248/129; 248/121; 248/150; 248/309.1; 248/316.5
(58) Field of Classification Search
CPC .................................................. A61M 5/1415
USPC .............. 248/539, 121, 129, 150, 357, 309.1, 248/313, 316.1, 316.5; 211/4, 5, 17, 60.1, 211/85.6, 85.13; 280/651, 654, DIG. 6
See application file for complete search history.

(56) References Cited

U.S. PATENT DOCUMENTS

| | | | |
|---|---|---|---|
| D45,770 S | | 5/1914 | Shaw |
| 1,612,148 A | * | 12/1926 | Oettinger .................... 211/85.6 |
| 2,583,114 A | | 1/1952 | Monteith |
| 2,794,612 A | | 6/1957 | Clifton |
| 3,437,296 A | * | 4/1969 | Hinz .......................... 248/354.5 |
| 3,719,789 A | | 3/1973 | Harnden, Jr. |
| 4,251,044 A | | 2/1981 | Olson |
| 4,332,378 A | | 6/1982 | Pryor |
| 4,341,381 A | | 7/1982 | Norberg |

(Continued)

FOREIGN PATENT DOCUMENTS

WO    WO 2008/085698    7/2008

OTHER PUBLICATIONS

International Search Report and Written Opinion, Corresponding to International Application No. PCT/US2007/088433, Mailed Aug. 7, 2008.

(Continued)

*Primary Examiner* — Anita M King
(74) *Attorney, Agent, or Firm* — Lathrop & Gage LLP

(57) ABSTRACT

Provided are holders for compactly storing infusion management systems to surfaces. In an embodiment the holder apparatus has a head portion for receiving and infusion management system trunk portion and a foot for receiving an apex portion of the infusion management system. The holder apparatus may be mounted to a wall so that the infusion management system is compactly stored and then mounted against the wall, thereby dramatically decreasing the storage footprint of the systems when not in use, without sacrificing the ability to conveniently and rapidly deploy the system when needed. Also provided are infusion management systems configured for use with the holder apparatus and related methods of storing the system.

18 Claims, 19 Drawing Sheets

(56) References Cited

U.S. PATENT DOCUMENTS

| | | | |
|---|---|---|---|
| 4,725,027 | A | 2/1988 | Bekanich |
| 4,744,536 | A | 5/1988 | Bancalari |
| 4,807,837 | A | 2/1989 | Gawlik et al. |
| 4,867,273 | A | 9/1989 | Schaevitz |
| 4,892,279 | A | 1/1990 | Lafferty et al. |
| 4,905,944 | A | 3/1990 | Jost et al. |
| 4,907,794 | A | 3/1990 | Rose |
| D310,570 | S | 9/1990 | Wells |
| 5,167,389 | A | 12/1992 | Reimers |
| 5,411,044 | A | 5/1995 | Andolfi |
| 5,458,305 | A | 10/1995 | Woodward |
| 5,479,953 | A | 1/1996 | Pasulka |
| 5,526,894 | A | 6/1996 | Wang |
| D385,348 | S | 10/1997 | Ward et al. |
| 5,704,577 | A | 1/1998 | Gordon |
| 5,772,162 | A | 6/1998 | Lin |
| 6,056,249 | A | 5/2000 | Fillon |
| D434,495 | S | 11/2000 | Whalen |
| 6,161,850 | A | 12/2000 | James et al. |
| D436,167 | S | 1/2001 | Ebert |
| 6,296,260 | B1 | 10/2001 | Schiavone |
| 6,296,263 | B1 | 10/2001 | Schultz et al. |
| D479,164 | S | 9/2003 | Wu |
| 6,619,599 | B2 | 9/2003 | Elliot et al. |
| 6,698,789 | B2 | 3/2004 | Reimers et al. |
| 6,839,939 | B2 | 1/2005 | Donakowski |
| D503,909 | S | 4/2005 | Tolfsen et al. |
| 6,969,031 | B2 | 11/2005 | Ugent et al. |
| 6,983,915 | B2 | 1/2006 | Adelman |
| D519,423 | S | 4/2006 | Tolfsen |
| 7,065,812 | B2 | 6/2006 | Newkirk et al. |
| 7,278,615 | B2 * | 10/2007 | Schubert et al. ........... 248/125.2 |
| D568,467 | S | 5/2008 | Cottone |
| 7,634,824 | B2 | 12/2009 | Gramkow et al. |
| D622,377 | S | 8/2010 | Jackson |
| D630,731 | S | 1/2011 | Schmutzer et al. |
| 8,136,773 | B2 | 3/2012 | Schmutzer et al. |
| 8,534,616 | B2 * | 9/2013 | Schmutzer et al. ........ 248/125.8 |
| 2003/0178538 | A1 | 9/2003 | Hasloecher et al. |
| 2005/0139736 | A1 | 6/2005 | Breda et al. |
| 2005/0230573 | A1 | 10/2005 | Ligertwood |
| 2008/0156946 | A1 | 7/2008 | Schmutzer et al. |
| 2008/0210831 | A1 | 9/2008 | Considine |
| 2012/0133111 | A1 * | 5/2012 | Schmutzer et al. ........... 280/651 |
| 2013/0270799 | A1 * | 10/2013 | Schmutzer et al. ........... 280/651 |

OTHER PUBLICATIONS

Office Action and Response, Corresponding to U.S. Appl. No. 11/961,834, Mailed Beginning May 12, 2011.

* cited by examiner

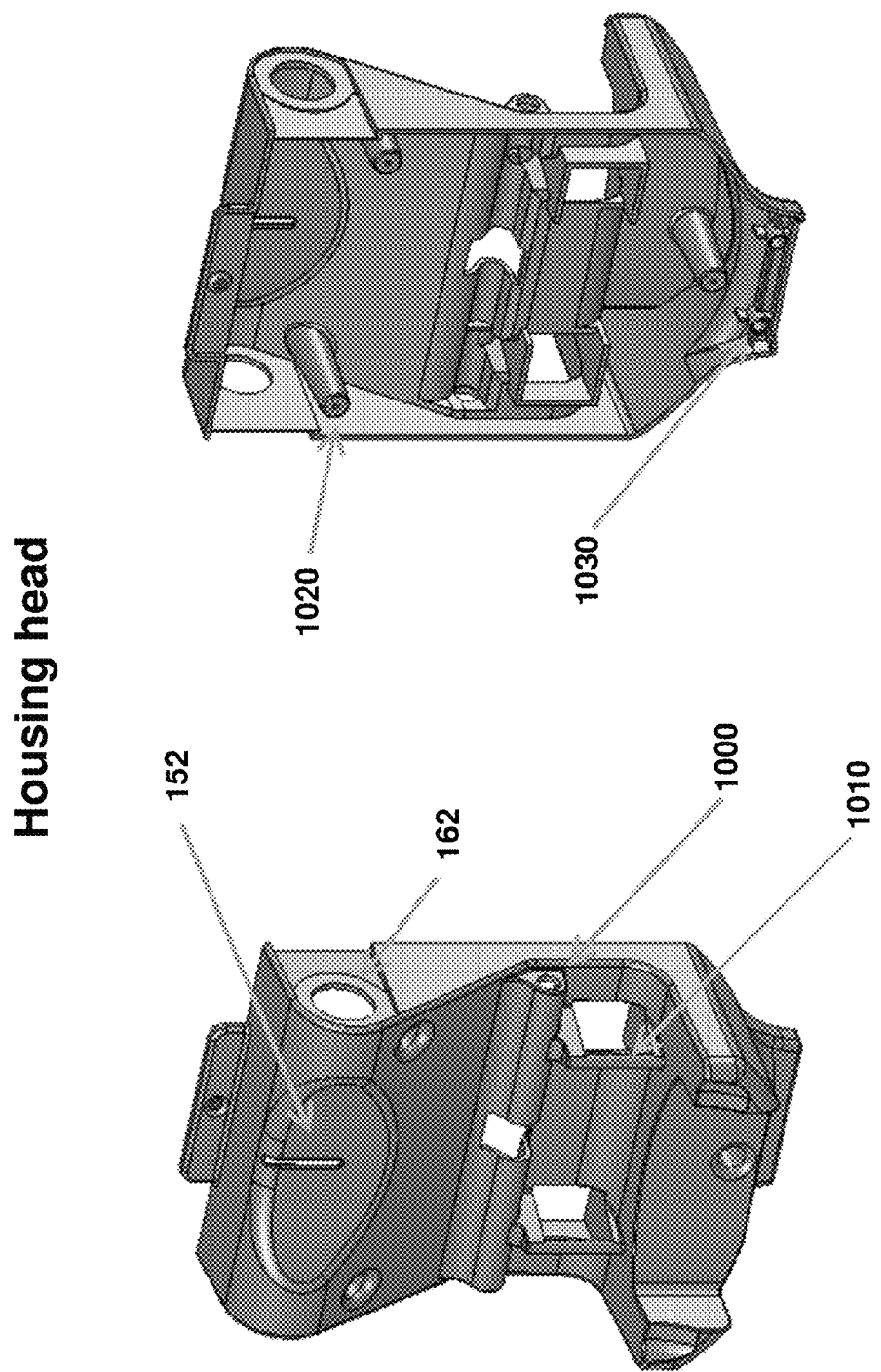

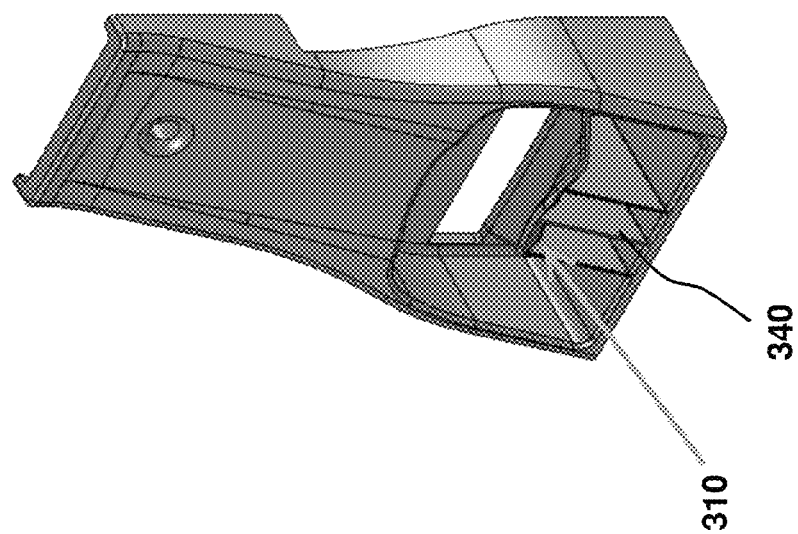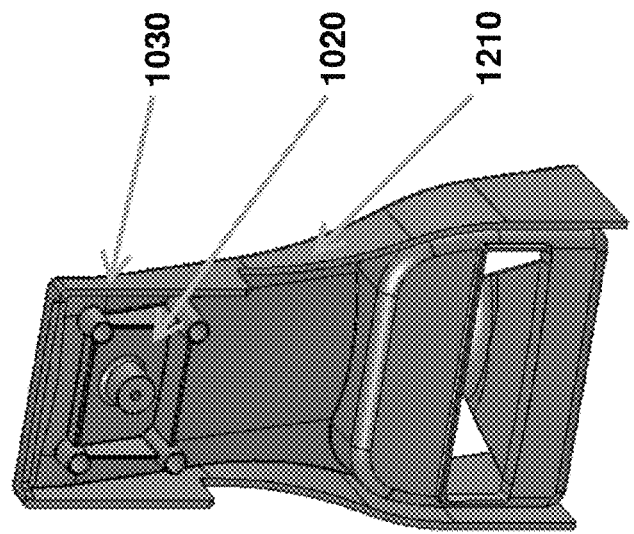
Figure 12

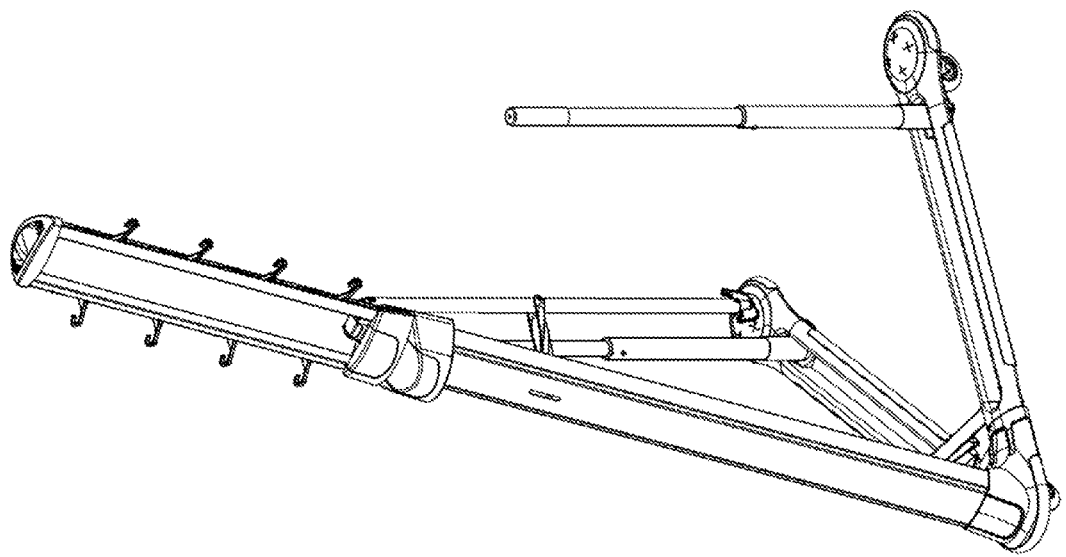
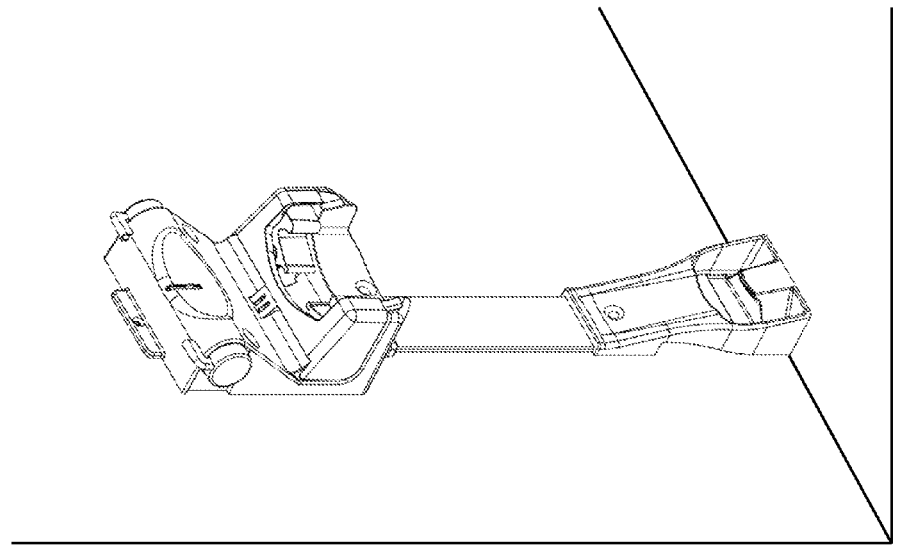
Figure 17

INFUSION MANAGEMENT SYSTEM AND HOLDER

CROSS-REFERENCE TO RELATED APPLICATIONS

This application claims benefit of U.S. Provisional Patent App. No. 61/301,843 filed Feb. 5, 2010, which is hereby incorporated by reference to the extent not inconsistent with the disclosure herein.

BACKGROUND OF THE INVENTION

Despite the ongoing and growing demand for patient mobility, load capacity, multi-functionality, safety and stability, the basic IV pole design has not significantly changed since the 1920's. Thus, it is not surprising that the basic IV pole design is obsolete and represents, at best, a nuisance and in many situations a hazard for both patients and patient caregivers, including hospital personal. Not uncommonly, the basic IV pole is prone to tipping, especially on carpets and when encountering bumps or any surface transitions (e.g., elevator, carpet/hard surface transition, doorways, etc.).

As the complexity of medical care has increased, so has the number, amount and weight of medical materials needed to be connected to a patient, including a patient that is to ambulate. In fact, depending on the medical intervention, a single patient may have a dozen or more infusions proceeding simultaneously. This makes the conventional IV pole rather top heavy and prone to tipping in response to the slightest perturbation. Accordingly, IV poles are involved in a significant percentage of injury-causing falls in hospital settings. Each year, it is estimated that about 1 million or more patients will fall in acute care settings and that about 30% will incur moderate-severe injuries, burdening the healthcare system with a significant additional cost. This problem is further exacerbated as Medicare no longer pays extra for specific conditions that could be avoided if the hospital followed proven preventive procedures or common-sense precautions. Medicare no longer pays hospitals for extra care given to patients injured by falls in the hospital and many private insurers are following Medicare's lead.

There is, therefore, a need in the art for superior alternatives to conventional intra-venous (IV) poles that mount infusion pump devices, IV bags, and other medical materials that provides safe ambulation for patients undergoing IV therapy. Various alternatives are described in U.S. Patent Publication No. 2008/0156946.

An additional drawback to the IV poles currently used is that they are very difficult to store. Generally, when not in use they are clustered together in a storeroom (or an unused patient room converted to a storage room), or at the end of a hall. This clustering results in a jumble of devices that may be difficult to access when a pole is needed, as well as occupying valuable hospital space that could be better utilized. This is not a simple problem because a typical hospital likely owns hundreds of IV poles.

Even in smaller settings, such as doctors' offices, the presence of only a couple of IV poles can present serious storage issues. The apparatus holders for IMS, IMS units, and related methods provided herein address the need for a safe, stable and reliable infusion management system that addresses the deficiencies identified herein, but also provide compact storage and ready deployment by a single caregiver.

SUMMARY OF THE INVENTION

In the medical field, conventional IV pole systems that are capable of simultaneously supporting medically-required items without adversely affecting patient mobility are extremely limited, as discussed in U.S. Pat. Pub. No. 2008/0156946. Provided herein are devices, systems and methods that address, among others, the lack of storability of those conventional IV poles. In particular, disclosed herein is an infusion management system unit (IMS) capable of extreme compactability and storage that is convenient, safe and reliable. Furthermore, provided are holders that can secure and store the IMS in locations that minimize the required storage footprint and in locations that do not interfere with patient care, while ensuring the IMS is readily available to the caregiver and/or the patient. Methods related to storing an IMS and an IMS and holder in combination, are also provided.

In an embodiment, the invention is an apparatus for mounting an infusion management system to a wall, such as a holder capable of reversibly holding the IMS, wherein the holder is connected to the wall. In an aspect, the apparatus comprises a head comprising a holder for reversibly mounting a trunk portion of the infusion management system to the head, and a foot comprising an apex catch for reversibly mounting an apex region of the infusion management system to the foot. Optionally, the head and the foot are individual components that are not directly attached to each other. Optionally, the head and the foot are connected to each other, such as by a direct connection, or by a third component such as a neck. Optionally, the head and the foot are formed from a single integrated body.

In an embodiment, the head's holder comprises a pair of vertically opposed flappers that reversibly mounts a trunk hold portion of the infusion management system to the head. As used herein, "trunk hold portion" refers to the configuration where a specific location of the trunk is secured by physical contact with the holder, rather than the entire trunk. In an aspect, the trunk outer surface is shaped, and the flappers that make physical contact with the trunk outer surface to hold the trunk have a shaped flapper contact surface correspondingly shaped to conform to the trunk outer surface shape for additional contact surface area. For example, for a circular outer surface trunk shape, the flapper contact surface is correspondingly circular shaped (e.g., the contact surface is provided as a portion of a circle). Similarly, any arbitrary trunk outer surface shape can dictate the shape of the flapper contact surface. In certain embodiments where it is desirable to minimize the likelihood of rotational trunk slip, it is preferred the trunk not be circular, but instead have extended or elongated edges that may be positioned in the flapper, without unduly hindering the ability of the flappers to reliably and easily capture and/or release the IMS trunk.

In an embodiment, the holder further comprises a locking hood operably connected to the flappers, wherein in a stored configuration the locking hood engages the flappers to secure the flappers in a closed position, and in an empty configuration the locking hood is not engaged to the flappers and the flappers may be positioned in either an open or closed configuration. There are many configurations that can achieve this locking hood and flapper operability to achieve holder functionality. For example, the flappers may be manually closed and a shaped locking hood placed over the flappers to ensure they do not accidentally release. To open the flappers, the locking hood may be removed. Alternatively, the locking hood may be engaged by the user or in response to a force generated on the head by introduction of an IMS to the head. Alternatively, the flappers may be secured directly into place without a locking hood.

In one embodiment, the apparatus further comprises a flapper spring (or, equivalently, a tensioning element) having a first end connected to a first flapper and a second end connected to a second flapper, wherein the flapper spring is in a stretched configuration when the locking hood is engaged with the pair of vertically opposed flappers and is in a relaxed configuration when the locking hood is not engaged with the pair of vertically opposed flappers. Accordingly, to prevent the flappers from relaxing into an open configuration once closed, locking hood is placed over the flappers. A person skilled in the art will appreciate other configurations may achieve similar functionality, including springs that act to close flappers and locking hoods that ensure flappers are unlocked as desired.

In an aspect, the holder apparatus further comprises an alignment holder. The alignment holder can help facilitate positioning of the IMS with the holder, and particularly the trunk and the head. The alignment holder may comprise a rotatable release hook connected to the head and a rotatable release handle rotatably connected to the rotatable release hook. "Rotatably connected" refers to the rotation of one element resulting in rotation of a second element. In this aspect, rotation of the release handle rotates the rotatable release hook to align and secure an infusion management system to the head of the holder, or to facilitate removal of an infusion management system from the head of the holder, such as by interaction with an actuation slot in the trunk. In an aspect, engagement of the release hook with the actuation slot activates or pulls a release mechanism in the infusion management system that permits the base arms to rotate to and from a stowed state. Accordingly, for safety during use of the IMS the base arms, in an aspect, can only rotate relative to the trunk when the actuation slot is engaged, such as by engagement of the wall mount release hook with the actuation slot to pull a release mechanism in the actuation slot of the IMS.

In an embodiment, a shaft is connected to the rotatable release hook and to the rotatable release handle, so that a user rotating the release handle generates rotation in the shaft and corresponding rotation in the release hook.

In an aspect, the apparatus further comprises a guide face having a surface that substantially conforms to a trunk surface of the infusion management system and a release hook slot positioned in the guide face, wherein the rotatable release hook at least partially extends through the release hook slot. In an embodiment, the guide face surface is shaped or contoured to conform to the trunk surface that is to-be-positioned adjacent to the guide face surface. For example, the guide face surface may be at least partially concave to accommodate a convex shaped trunk surface. Such a configuration facilitates intimate contact between the trunk surface and the head.

In another embodiment, the apparatus apex catch comprises an opening and an apex mount for securing the infusion management system apex region in the opening, including an apex region having a mountable protrusion capable of being secured by the apex catch and opening in the foot.

In an aspect, the foot comprises a tapered body, the tapered body having minimum taper at a top end and a maximum taper at a bottom end, wherein the apex catch is at least partially positioned in the bottom end.

Any of the holders provided herein optionally further comprise a neck that connects to the head and the foot, wherein the neck has a first end connected to the head and a second end connected to the foot.

Any of the holders provided herein further comprise fasteners for fastening the head, the foot, or both the head and the foot to a wall.

In an aspect, any of the holder apparatus disclosed herein further comprise an infusion management system operably connected to the apparatus, wherein the infusion management system has a trunk reversibly connected to the head and an apex region reversibly connected to the foot. In an embodiment, the infusion management system has an alignment or an actuation slot in the trunk for reversibly engaging the rotatable release hook.

In another embodiment, the invention relates to, in combination, a holder apparatus and an IMS mounted thereto, such as a holder apparatus disclosed herein and an infusion management system having a trunk. The infusion management system comprises a trunk having a bottom end connected to an apex region and a top end that is at the opposite end of the trunk from the bottom end. A movable crown (for supporting various medical-related items, such as fluid bags) is operably connected to the trunk. The movable crown has a bottom crown end and a top crown end, with a longitudinal rail connecting the bottom crown end to the top crown end. In this manner, the length of the movable crown generally corresponds to the longitudinal length of the rails (plus the height of each of the crown). In this aspect, "operably connected" refers to the ability of the movable crown to move along the trunk axis and be positioned as desired ranging from longitudinal rails exposed above the trunk to longitudinal rails substantially or completely coincident with the trunk. In an aspect there is a single longitudinal rail. In an aspect there are two longitudinal rails, such as longitudinal rails that are vertically opposed and parallel to each other, with a portion of the trunk disposed and separating the rails when the movable crown is at least partially stored. In this manner, the longitudinal rails conform to the trunk outer surface. In an aspect there are more than two longitudinal rails. In an aspect, in a crown-stored configuration the movable crown spans a longitudinal crown portion of the trunk. In combination, the apex portion is positioned in the apex catch of the foot and a trunk hold portion positioned in the longitudinal crown portion of the trunk and is secured by the holder.

In another embodiment, the IMS further comprises an actuation slot in the trunk; wherein the release hook in the head is operably connected to the actuation slot. In this configuration, the release hook can assist in IMS alignment with the holder and also in storing and releasing the IMS from the apparatus and the holder in the head.

Also provided are various methods for reversibly mounting an infusion management system to a receiving surface. In an aspect, the method comprises providing an infusion management system comprising a trunk and an apex region and a surface mount (e.g., a holder apparatus), including any of the holder apparatus disclosed herein. In an aspect, the surface mount has a head connected to the surface, the head having a holder for receiving at least a portion of the infusion management system trunk (e.g., a trunk hold portion), and a foot connected to the surface, the foot having an apex catch for receiving at least a portion of the apex region of infusion management system. The at least a portion of the apex region is positioned in the apex catch and the head holder is secured around the trunk hold portion, thereby reversibly mounting the infusion management system to the receiving surface. In an aspect, the receiving surface is a wall, so that the IMS is secured to the wall via the surface mount. In another aspect the apex region comprises a mountable protrusion that is capable of being secured by the foot apex catch.

In an aspect, the infusion management system further comprises a pair of base arms rotatably connected to the trunk, the method further comprising rotating the pair of base arms to a position that is substantially parallel to the trunk. In this aspect, "substantially parallel" refers to the longitudinal axis of the base arm that is within about 10° of parallel to the longitudinal axis of the trunk, including within 5°, 1° or is parallel. Similarly, the movable crown may comprise one or two (or more) longitudinal rails that when stored, are substantially parallel or conforming to the trunk outer surface shape.

In another embodiment, the invention is an infusion management system, including infusion management systems configured for compact storage against a wall surface by an IMS holder. In an aspect, the IMS has a trunk, the trunk extending between bottom and top ends thereof, and an actuation slot positioned in a front face of the trunk. A movable crown system is movably connected to the trunk, particularly for movement in a direction along the trunk axis. The movable crown system comprises a top crown, a bottom crown and a pair of longitudinal rails, each rail having a first end that connects to the top crown and a second end that connects to the bottom crown. In this manner, movement of one element, such as the bottom crown, results in movement of the longitudinal rails and of the top crown. The movable crown has a deployed position and a stored position. The deployed position corresponds to the top crown in a position that is separated by a separation distance from the top of the trunk. The movable crown stored position corresponds to the top crown that is adjacent to the trunk top and longitudinal rails that do not extend beyond the trunk. Alternatively, the movable crown has a deployed position and a stored position, the deployed position corresponding to the bottom crown in a position that is beneath the actuation slot and the deployed position corresponding to the bottom crown that is above the actuation slot.

In an aspect, in a fully deployed position the bottom crown is adjacent to the trunk top end. In an aspect, in a fully stored position the top crown is adjacent to the trunk top end and the bottom crown is at a position on the trunk that is beneath the actuation slot position. "Fully", as used in this aspect, refers to the maximum extent of deployment or storage has been reached and no further motion in the respective direction is possible.

In an embodiment, the IMS further comprises a base comprising a first base arm and a second base arm, wherein one end of each of the base arms is connected to the trunk bottom end to form an apex region, and the base arms and the apex region define a two-sided base footprint, wherein the apex region comprises a nose cap having a front surface shaped to form a mountable protrusion.

BRIEF DESCRIPTION OF THE DRAWINGS

FIG. 7 is a schematic of the housing head portion of the holder.

FIG. 12 is a schematic of the holder foot portion showing a back (left panel) and front (right panel) view.

FIG. 17 illustrates a holder mounted to the wall and a deployed IMS in vicinity to the holder.

DETAILED DESCRIPTION OF THE INVENTION

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

Example 1

Wall-Mountable Holder for Storing an IMS

Figures 1A, 1B:
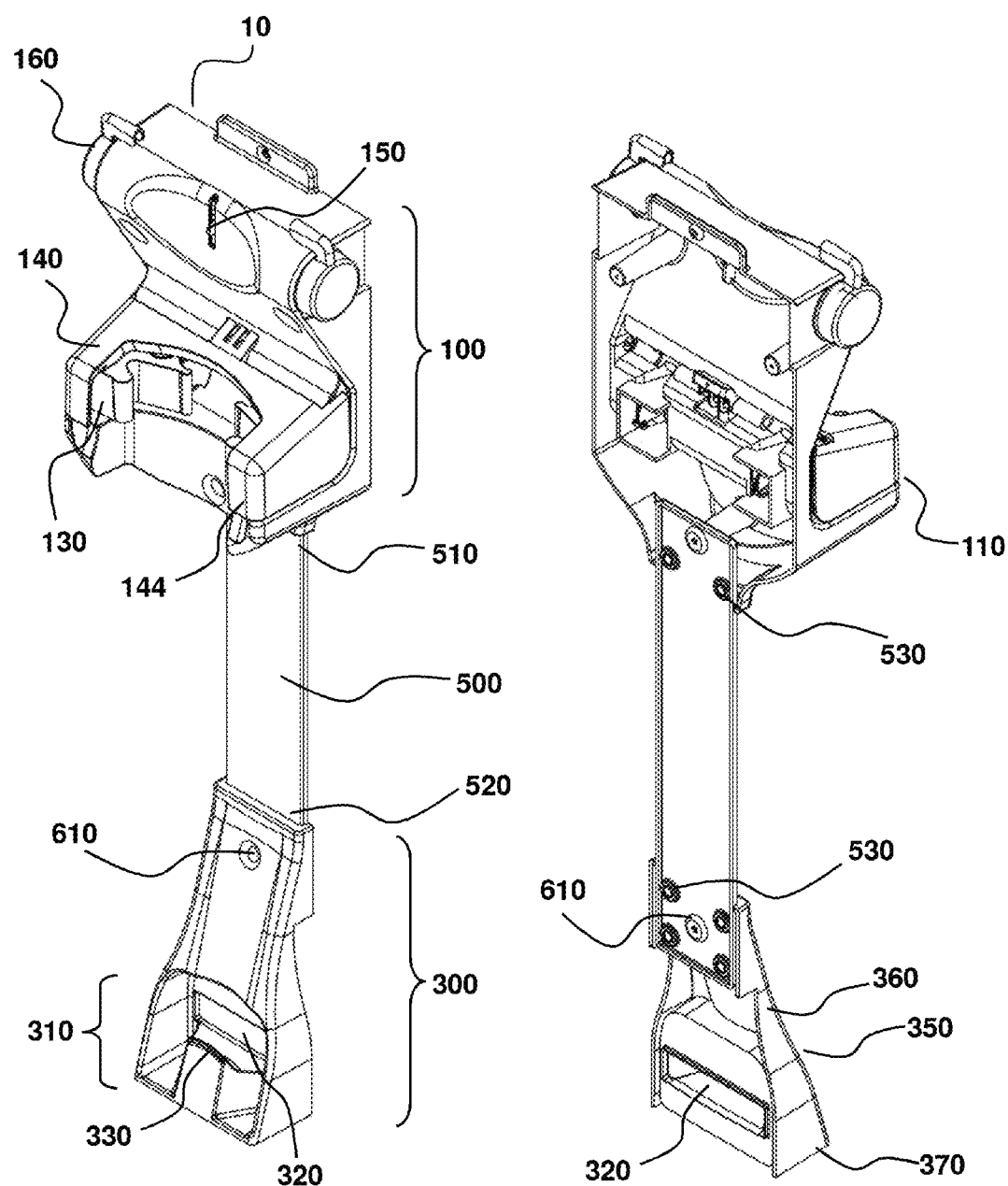
FIG. 1 is a schematic of one embodiment of a wall-mountable holder for an IMS. A is a front view and B is a rear view.
Figure 2:
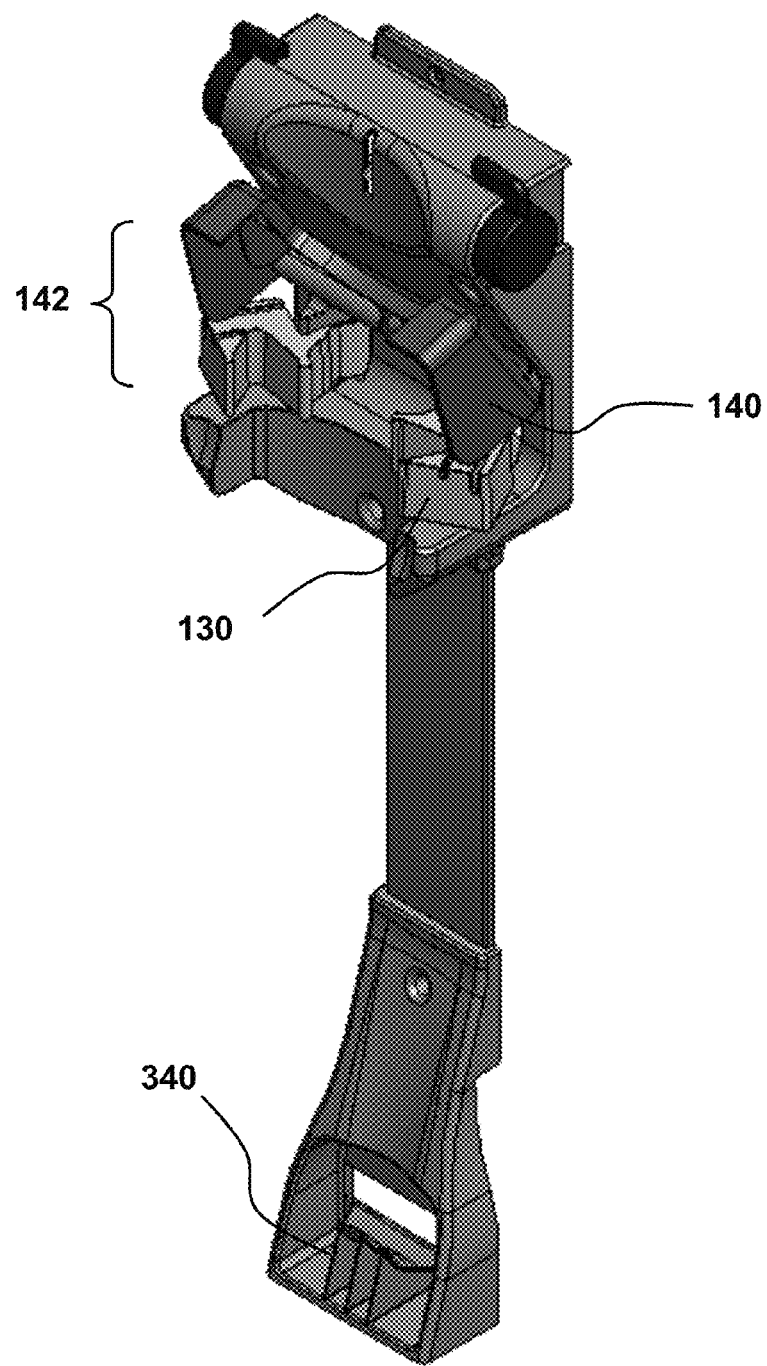
FIG. 2 is a schematic of an IMS holder with the flappers unlocked in an open configuration and ready to receive an IMS.

FIGS. 1-2 are schematics of a holder designed to be connected to a surface, such as a wall, and to which an IMS may be compactly and conveniently stored. In this embodiment, the apparatus holder 10 comprises a head 100, a foot 300, and a neck 500 that is connected to the head at a neck first end 510 and to the foot at a neck second end 520, such as at connection points or fasteners 530 at ends 510 and 520. Neck 500 is an optional component that can be used to provide additional structural support to the overall holder 10 and to assist in positioning the head 100 and foot 300 and, in particular, facilitate precise separation between those portions to ensure good fit to an IMS that is to be mounted to holder 10.

In operation, the head 100 functions to reliably secure a trunk portion of the IMS, such as by a holder 110. In the embodiment illustrated in FIG. 1, the holder 110 further comprises a pair of flappers 130 that are vertically opposed to each other. In particular, flapper pair 130 provide physical contact with a trunk of the IMS. Locking hood 140 is operably connected to the flappers 130. In this aspect, "operably connected" refers to elements that are connected in a manner to preserve functionality of each element and, accordingly, need not be directly connected to each other. In particular, in a position where the flappers 130 are engaged in a closed position (e.g., to securely hold the IMS trunk), locking hood 140 is positioned to prevent flappers 130 from opening. In contrast, when flappers 130 are desired to be in an open position (e.g., to facilitate release of the IMS trunk from the head 100), locking hood 140 can be positioned so as to not engage or confine position of flappers 130 (see, e.g., FIG. 2). FIG. 1 shows the locking hood and flappers in an engaged or closed position 144 and FIG. 2 shows an open configuration 142. Rotatable release hook 150 provides additional functionality to further facilitate releasable connection between the IMS and the holder.

Foot 300 is configured to receive the nose or apex region of an IMS. In the illustrated embodiment of FIG. 1, the foot has an apex catch 310 having an opening 320 and an apex mount 330 for reliably supporting and securing the bottom apex portion of the stored IMS to the foot. The foot may be configured to have a tapered body 350 having a top end 360 with a minimum taper and a bottom end 370 having a maximum taper.

Holder 10 can be mounted to a surface, such as a wall surface, by any means known in the art, such as by adhesives or fasteners. As desired, fastener holes 610 may be positioned through both head and neck, foot and neck, head only, foot only, neck only, or any combination thereof. As explained further in Example 2, it is important that the configuration and positioning of the head 100 and foot 300 relative to each other be matched to the IMS to ensure reliable connection between apparatus 10 and the IMS and also the apparatus 10 and the support surface (e.g., a wall) to which the holder is connected.

Example 2

IMS Configured for Use with the Holder of Example 1

The holder may be configured and design to mate to any number of different pieces of equipment that compactly fold and present an available longitudinal axis for the holder. In an embodiment, the holder is for use with an IMS, including the IMS disclosed in U.S. Pat. Pub. No. 2008/0156946 (which is hereby specifically incorporated by reference for the IMS disclosed therein). In an embodiment, the holder is configured to hold any of the IMS provided herein, including the embodiment illustrated in FIGS. 3-5.

Figure 3:
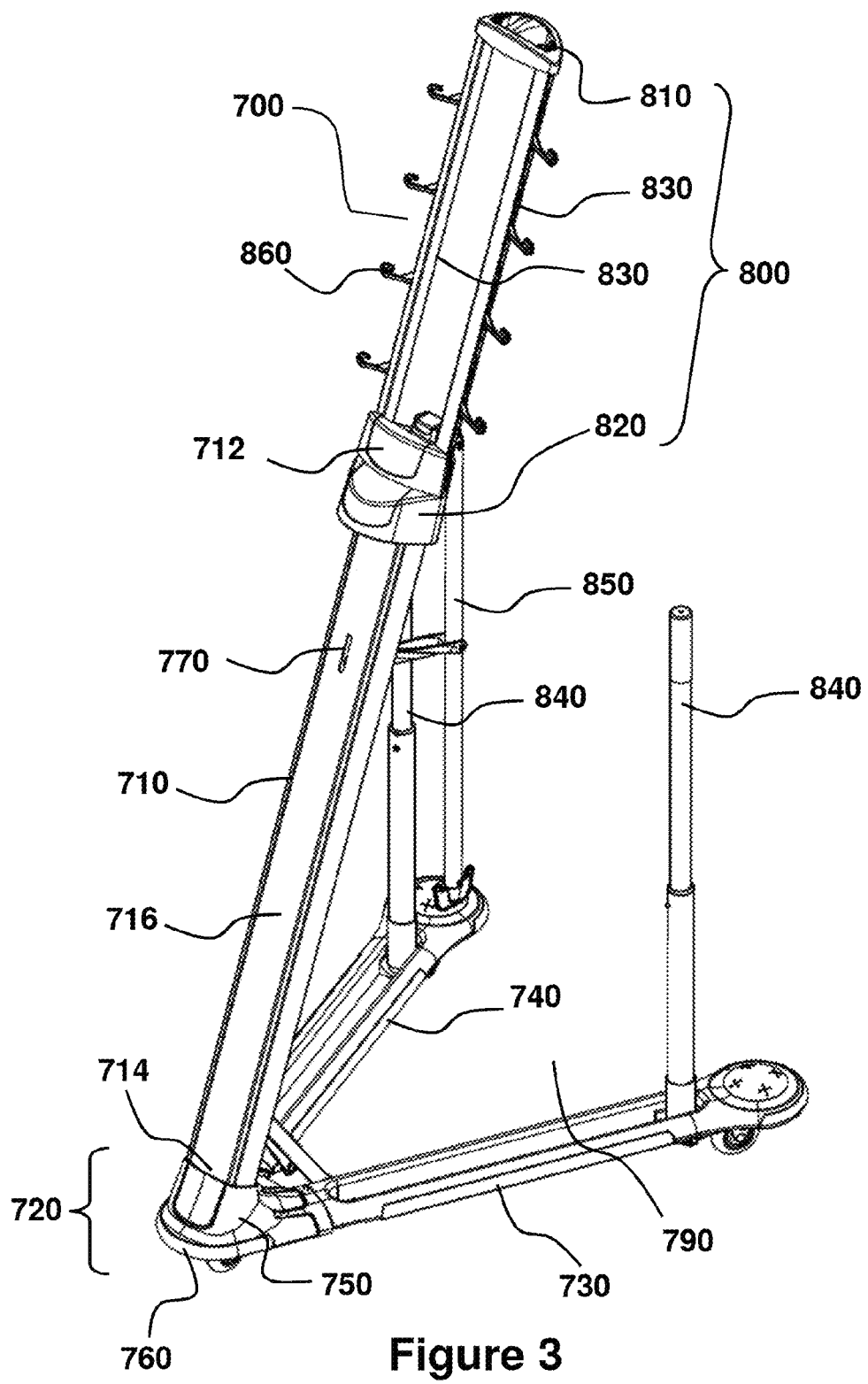
FIG. 3 is a schematic of an IMS in a fully-deployed configuration.

In an embodiment, the IMS is configured for stability and maneuverability, even under a heavy load. Furthermore, the IMS is capable of being compactly stored when not in use when connected to the holder apparatus disclosed herein. Referring to FIG. 3, IMS stability is achieved by providing a relatively large base footprint 790 formed by base arms 730 and 740 and a trunk 710 angled to ensure the center of mass of the system is centrally positioned relative to the base footprint. Trunk 710 is operably connected, either directly or indirectly, to various elements such as hooks 860 or pump mount 850 from which medical instruments or compositions can be supported.

FIG. 3 is an IMS that is fully deployed. In a fully deployed position each of the deployable elements, including movable crown system 800 (comprising top crown 810, bottom crown 820, and crown longitudinal rails 830), operation handles 840, pump mount 850, hooks 860, and base arms 730 and 740, are deployed and/or accessible. In contrast, various elements are optionally capable of being compactly stored as illustrated in FIG. 4, where the hooks are removed or stored in a recess of the longitudinal rail and the operational handles 840 are received in a recess or passage of the base arms 730 and 740 and FIG. 5.

Figure 4:
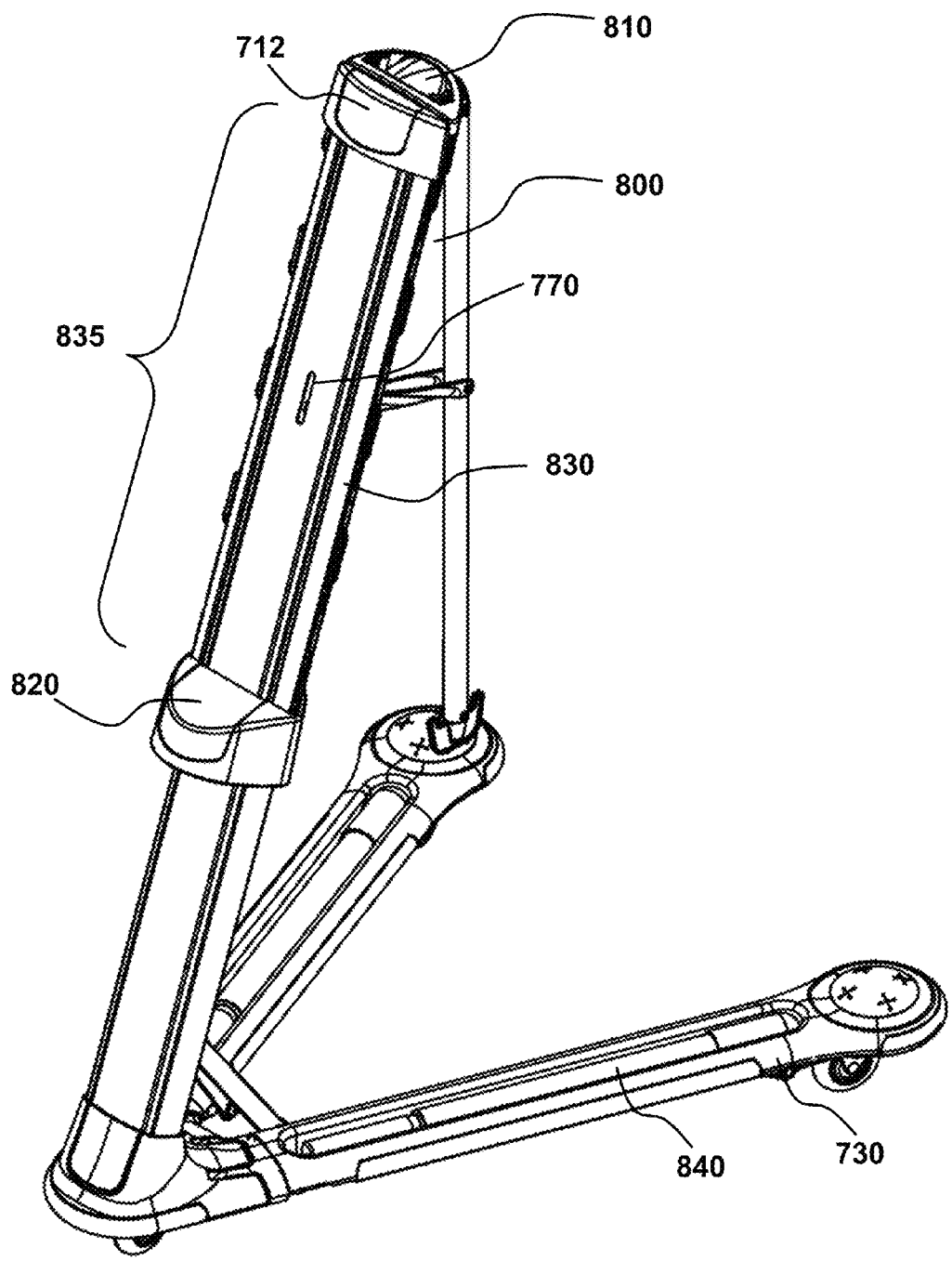
FIG. 4 is a schematic of an IMS with the movable crown and handle arms in a fully-stored configuration.

FIG. 4 shows the crown system 800 in a fully stored position, where the top crown 810 is adjacent to the trunk top 712, and in this example in physical contact with the trunk top 712. The portion of the trunk that is spanned by longitudinal rails 830 is referred to as the longitudinal crown portion 835 The movable crown system 800 can be positioned at various heights by positioning the bottom crown 820 at different longitudinal positions along the trunk longitudinal axis. Because the top crown 810 is rigidly connected to the bottom crown 820 by longitudinal rails 830, positioning bottom crown 820 provides corresponding positioning of top crown 810. The maximum movement of the bottom crown 820 to the lowest position on the trunk is constrained by the top crown 810 being prevented from further movement by the trunk top 712 (see FIG. 4). Aspects where the movable crown is not fully deployed or fully stored is referred to as "partially deployed."

Any means known in the art may be used to reliably position the movable crown system 800 with respect to the trunk 710. In one embodiment, the bottom crown 820 comprises a latch that when engaged generates a connective attachment (e.g., protrusions and slots including pins and holes) or a frictional force with the trunk, sufficient to prevent movement of the movable crown 800, even under relatively heavy load. When the latch is not engaged, the bottom crown, and corresponding entire crown system 800 is capable of moving along the trunk and trunk axis. In this manner, the movable crown system 800 may be deployed at various distances from the trunk top end 712.

Figure 5:
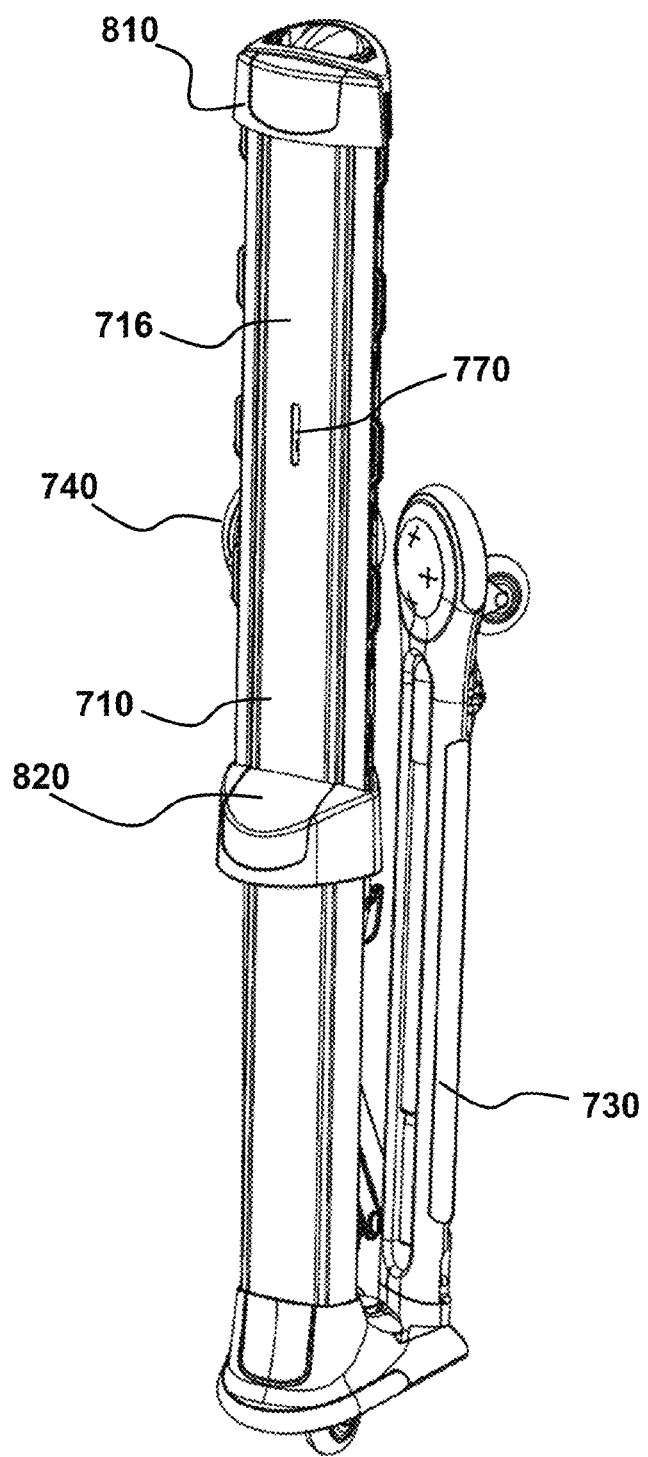
FIG. 5 is a schematic of an IMS in a fully-stored configuration.

When not in use, the IMS can be compactly stored by rotating base arms 730 and 740 to a position that is substantially parallel to the trunk 710, as shown in FIG. 5. Furthermore, to further facilitate connection with the holder 10, actuation slot 770 is positioned on the trunk front face 716 between the bottom crown 820 and top crown 810. In this configuration holder 10, and specifically head 100 and foot 300, can secure the IMS 700 (FIG. 6), such as against a wall to which the holder is mounted. In this manner, the IMS can be easily stored in a compact, but accessible manner. The arrow in FIG. 6B represents a force applied to remove the IMS from the holder.

Figure 19:
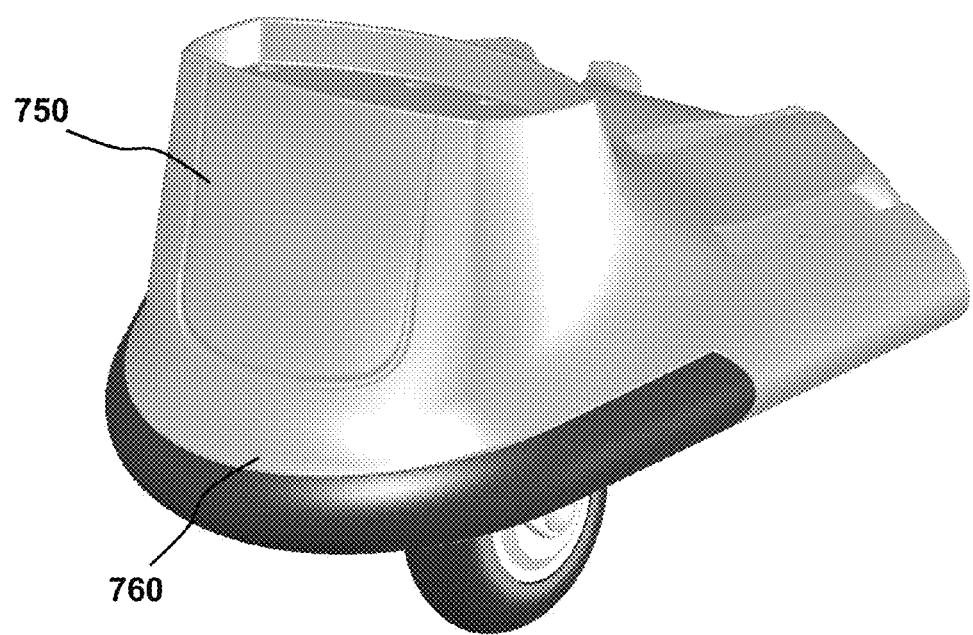
FIG. 19 Close-up view of the nose cone and apex region of the IMS.

Connection between the foot apex catch 310 of holder 10 and apex region 720 is facilitated by nose cap 750 illustrated in FIG. 19. The nose cap 750 of apex region 720 has a mountable protrusion 760 to further fit into foot 300 apex catch 310 and opening 320.

Example 3

Holder Head

FIGS. 7-10 illustrate an embodiment of the holder head 100. FIG. 7 is the housing portion of the head that accommodates various elements of the head. The left panel is a front view showing the release slot 152 for accommodating the rotatable release hook and a release handle surface 162 for accommodating a rotatable release handle 160 (shown in FIG. 8). The right panel is a back view. The housing is configured to provide various pivots, including hood pivot 1000 and flapper pivot 1010, for operably connecting the locking hood and the flappers. Various bosses, including mounting bosses 1020 and alignment bosses 1030, are provided to facilitate mounting and alignment of the head.

Figure 8:
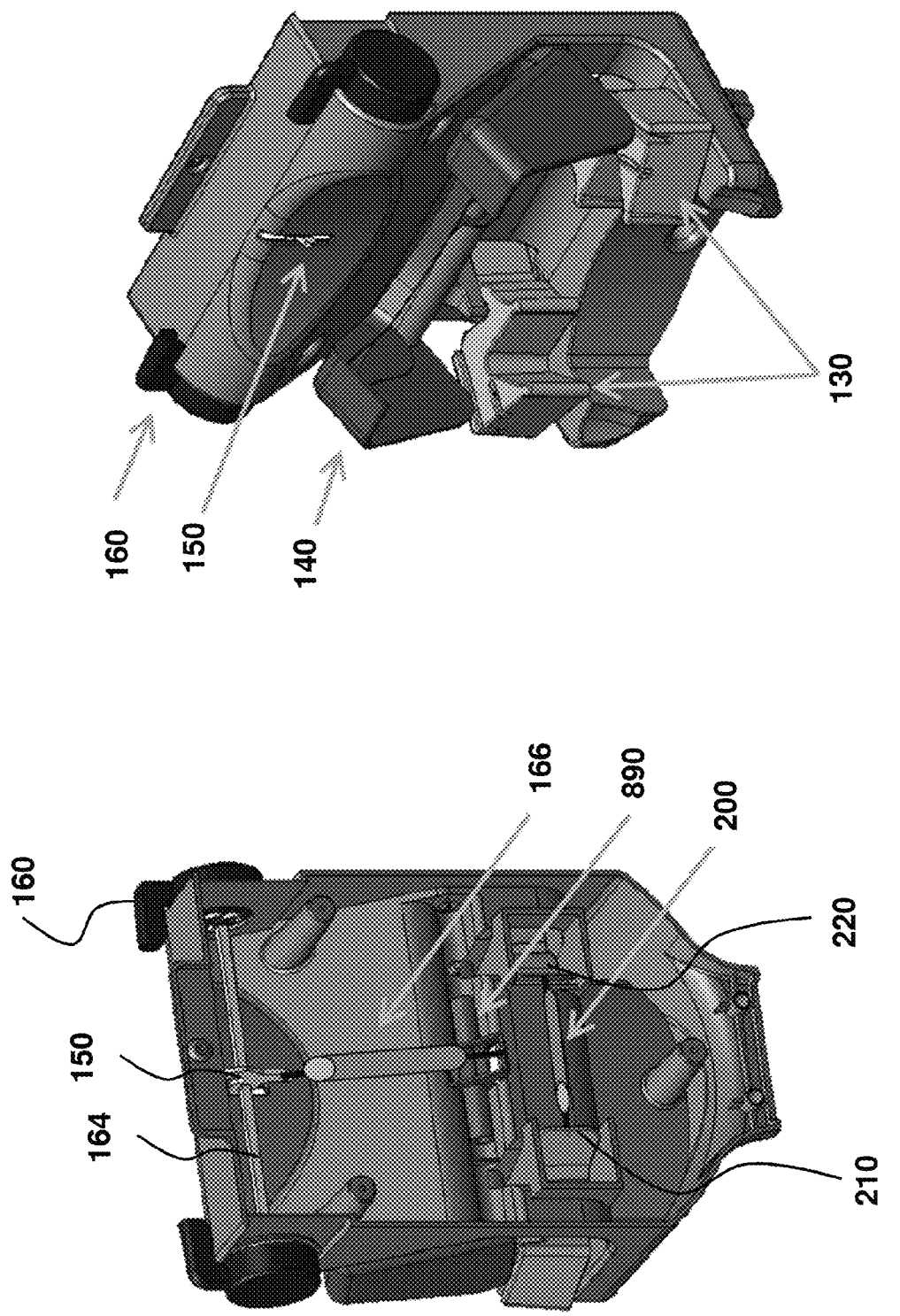
FIG. 8 is a schematic of a catch/release mechanism of the holder head.
Figure 9:
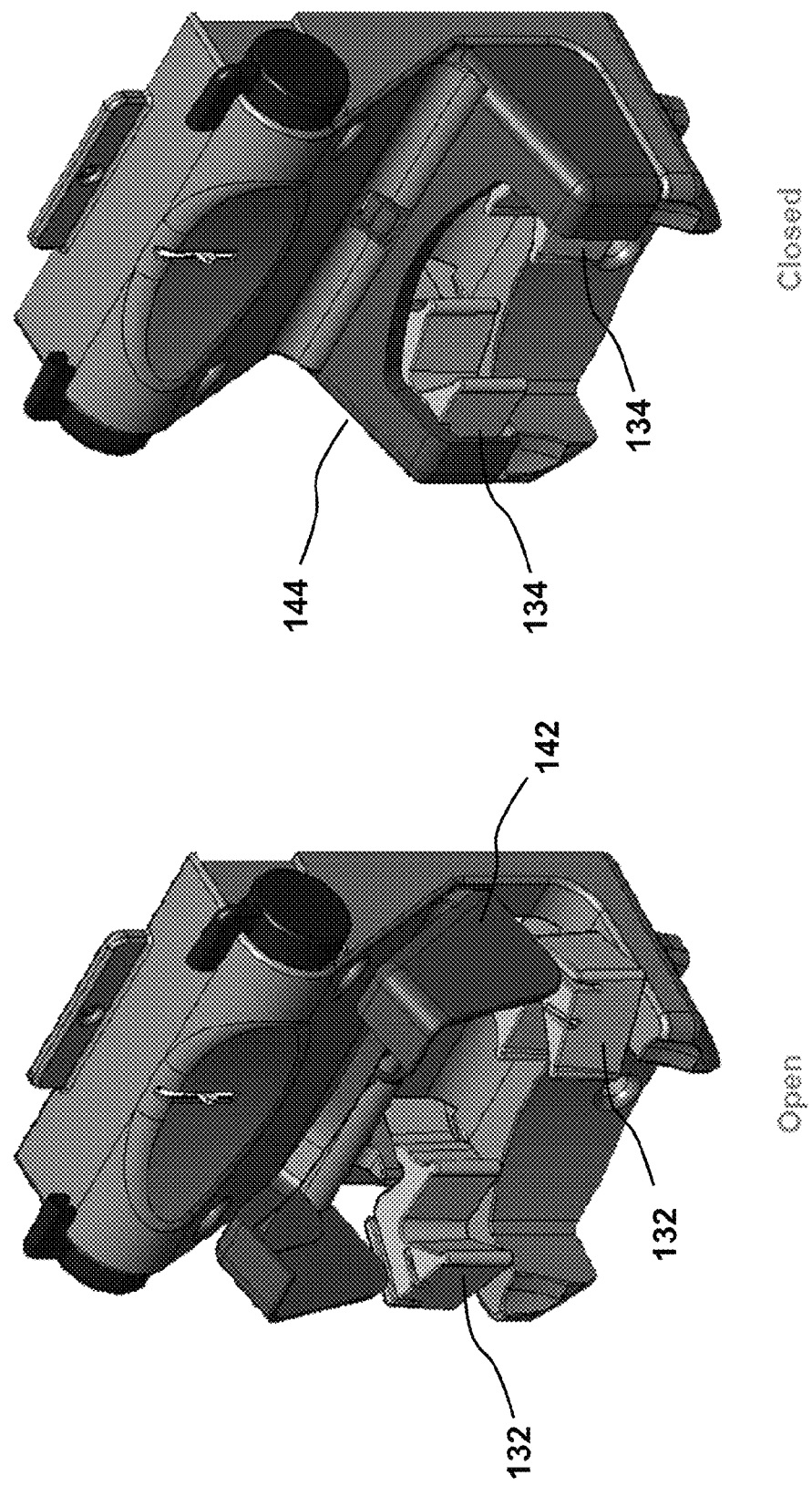
FIG. 9 is a schematic of the holder in an open (left panel) and a closed (right panel) configuration.

FIG. 8 illustrates the housing of FIG. 7 in combination with various elements for securing the IMS trunk. The front view (right panel) shows the release handles 160, rotatable release hook 150, locking hood 140, locking pin 890 and flappers 130 connected to the housing. Rotation of release handles by a user provides a corresponding rotation of the release hook. The pivot directions of the locking hood and flappers are perpendicular to each other and is one example of the interaction between the locking hood and flappers to provide a secure and reliable reversible connection between the trunk of the IMS and the holder. The back view of the head illustrates the use of various tension supplying devices, such as springs, for controlling the position of the flappers and the locking hood. In particular, a flapper spring 200 connected to one end of each of the flappers (e.g., first end 210 connected to first flapper and second end 220 connected to second flapper) normally operates to ensure the flappers are open and ready to receive the trunk portion of the IMS. This is illustrated in FIG. 9A. Engaging the locking hood from an open position 142 over the flappers into a locked or closed position 144, however, stretches the flapper spring 200 and brings the vertically opposed flappers from an open position 132 into a closed position 134, as illustrated in FIG. 9B. In an aspect, the release handles 160 is operably connected to the locking hood 140 via a shaft 164, release hook 150 and release spring 166 (see FIG. 8, back view). In this manner, rotation of release handle 160 releases locking hood 140, thereby opening flappers 130 by the resultant force generated by flapper spring relaxing from a stretched state to a less stretched or relaxed state. Accordingly, the trunk portion is ready to be released from the holder.

Figure 10:
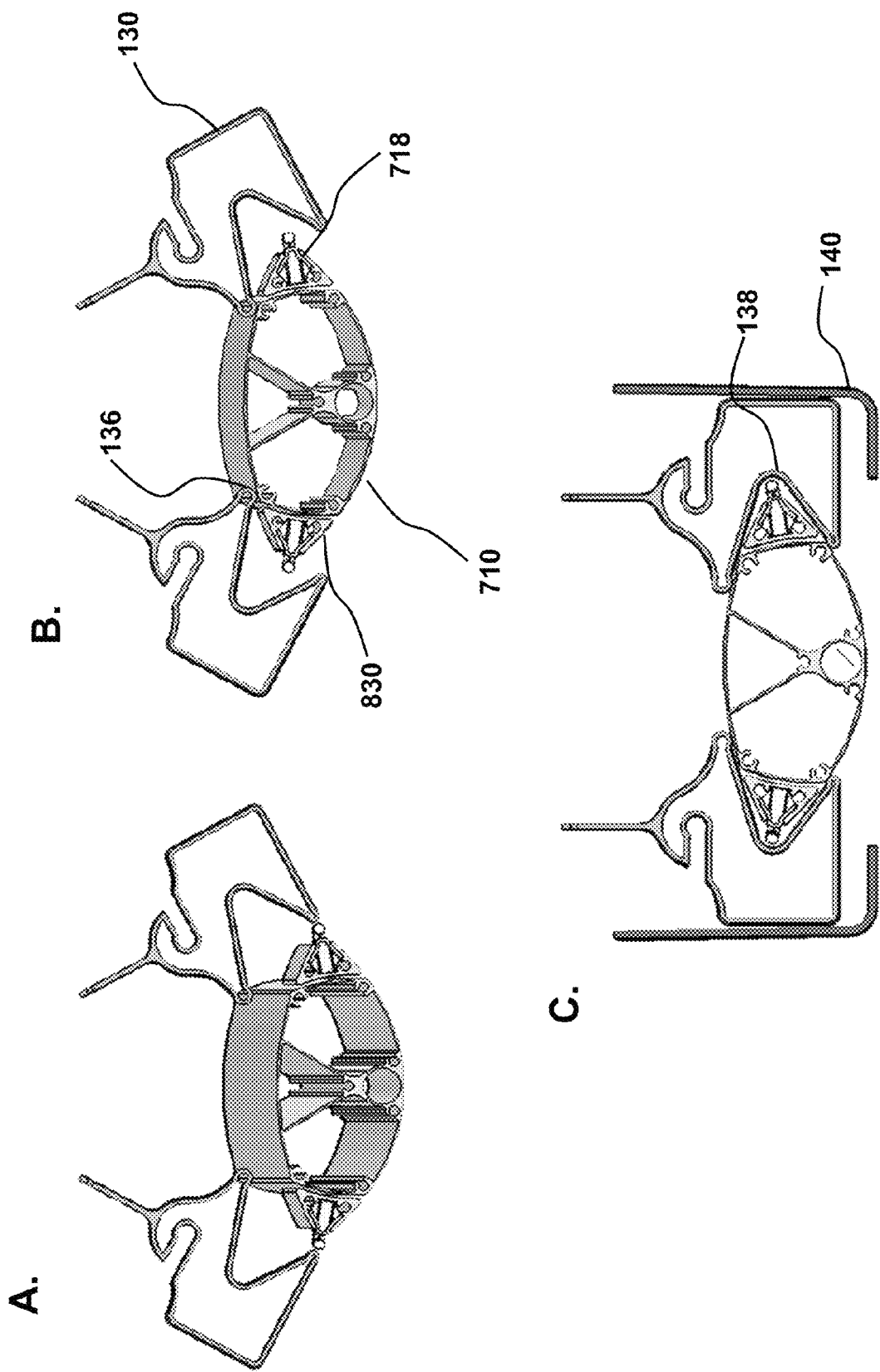
FIG. 10 is a schematic showing one embodiment of the catch/release mechanism as an IMS trunk portion is positioned in the holder head portion (A and B) and subsequently held by the flappers and locking hood of the catch mechanism (C).

FIG. 10 is a schematic overview of the trunk being positioned between the flappers 130 that are in an open configuration (top two panels) and then being secured by locking hood 140 that is locked over the flappers. The relative positioning of the pivot directions in a substantially orthogonal direction ensures the flappers cannot disengage without release of the locking hood. The cross-sectional view of the trunk 710, shows the outer trunk surface shaped to have elongated edges 718 when the longitudinal rails 830 are stored, with the flappers correspondingly shaped, to minimize torsional or rotational slip. In particular, when the trunk hold portion 780 is introduced to the holder, there is a flapper initial contact point 136 that forms into a contact area defined by the region of contact of the trunk hold portion corresponding to the flapper contact surface 138.

Example 4

Neck and Foot

Figure 11:
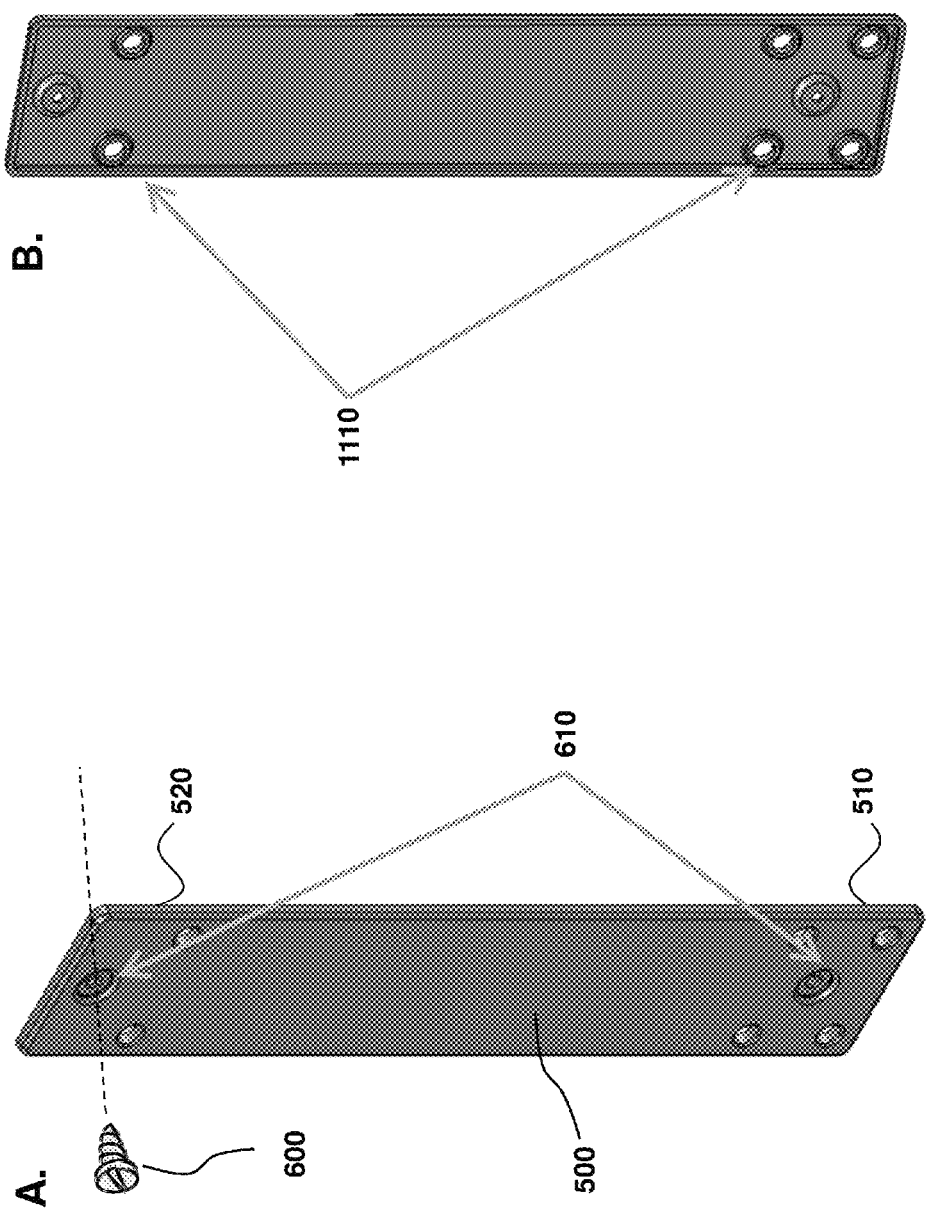
FIG. 11 is a schematic of a neck portion of the holder showing a front (A) and a back (B) view.

FIG. 11 is a front (left panel) and back (right panel) view of the neck 500 having first 510 and second 520 ends for connecting to the head and foot portions of the holder. Fasteners 600 may be introduced through fastener access passages 610 or mounting holes to mount the holder to the wall. Alignment holes 1110 assist with positioning and separation of the foot and head portions of the holder, such as with alignment bosses (shown in FIG. 12 for the foot and in FIG. 7 for the head).

One embodiment of a holder's foot portion is illustrated is FIG. 12 (back view in left panel and front view in right panel). The nose or apex catch 310 is configured to secure a portion of the IMS apex region, such as a mountable protrusion 760 (see FIG. 19) on the apex that mates with the shape of the foot opening formed by the apex catch. Additional structural support may be achieved by introducing struts 340 to the apex catch (see FIG. 2). Also indicated is a wall trim clearance 1210 (1"×8").

Example 5

Reversibly Mounting IMS to Holder

Figure 6A:
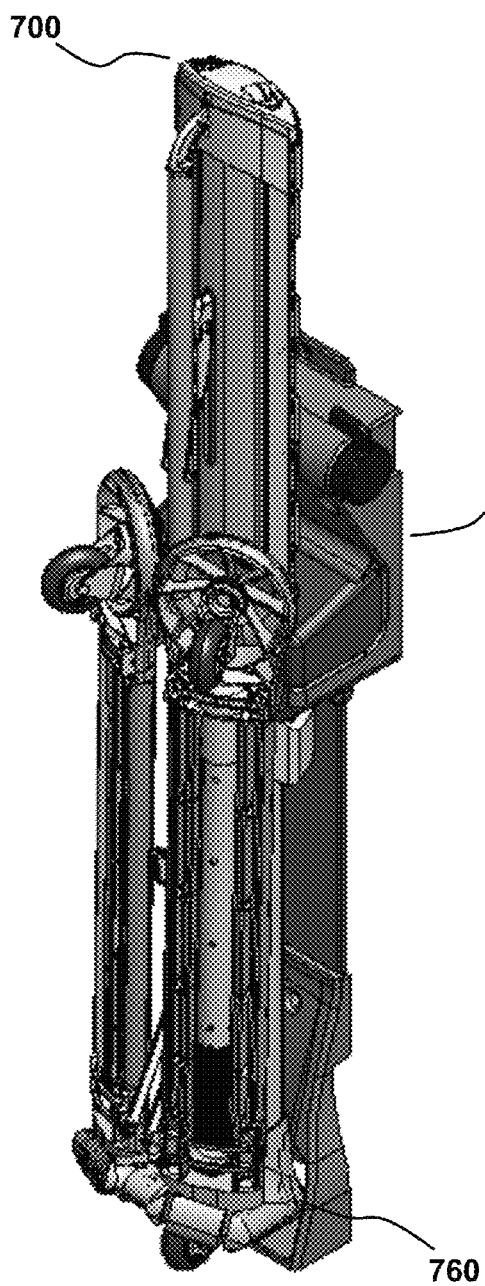
FIG. 6 is a schematic of an IMS in a fully-stored configuration and mounted to the holder. A is a perspective view and B is a side view. The arrow in B indicates the direction of a force for removing the IMS from the holder.
Figure 6B:
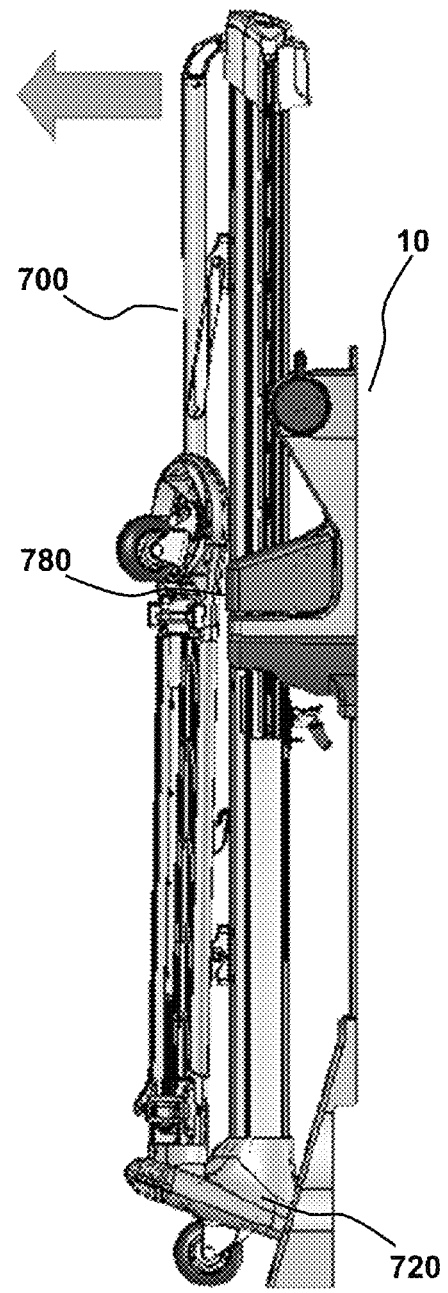
Figure 16:
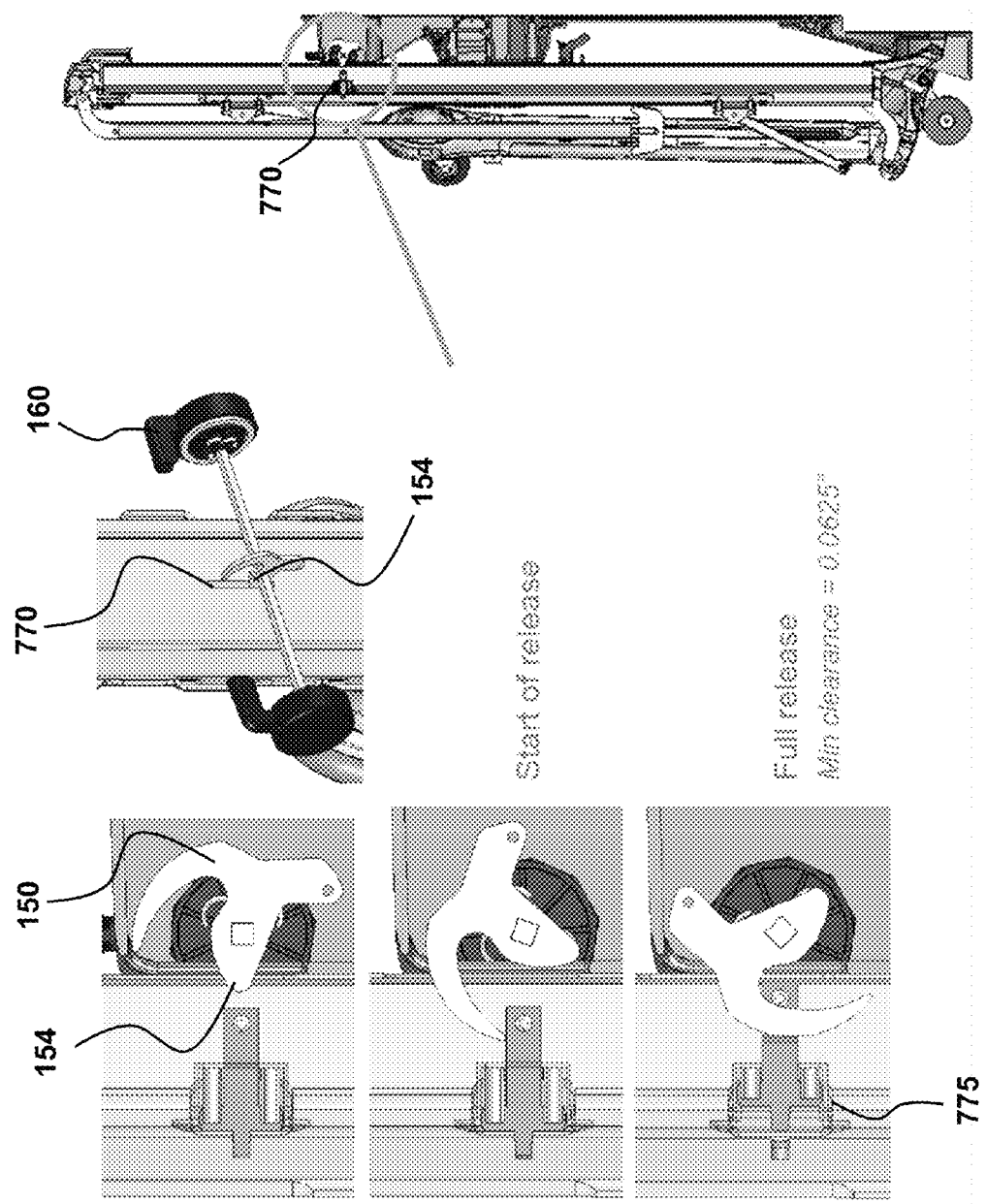
FIG. 16 is a schematic of the release hook engaging an IMS trunk.
Figure 18:
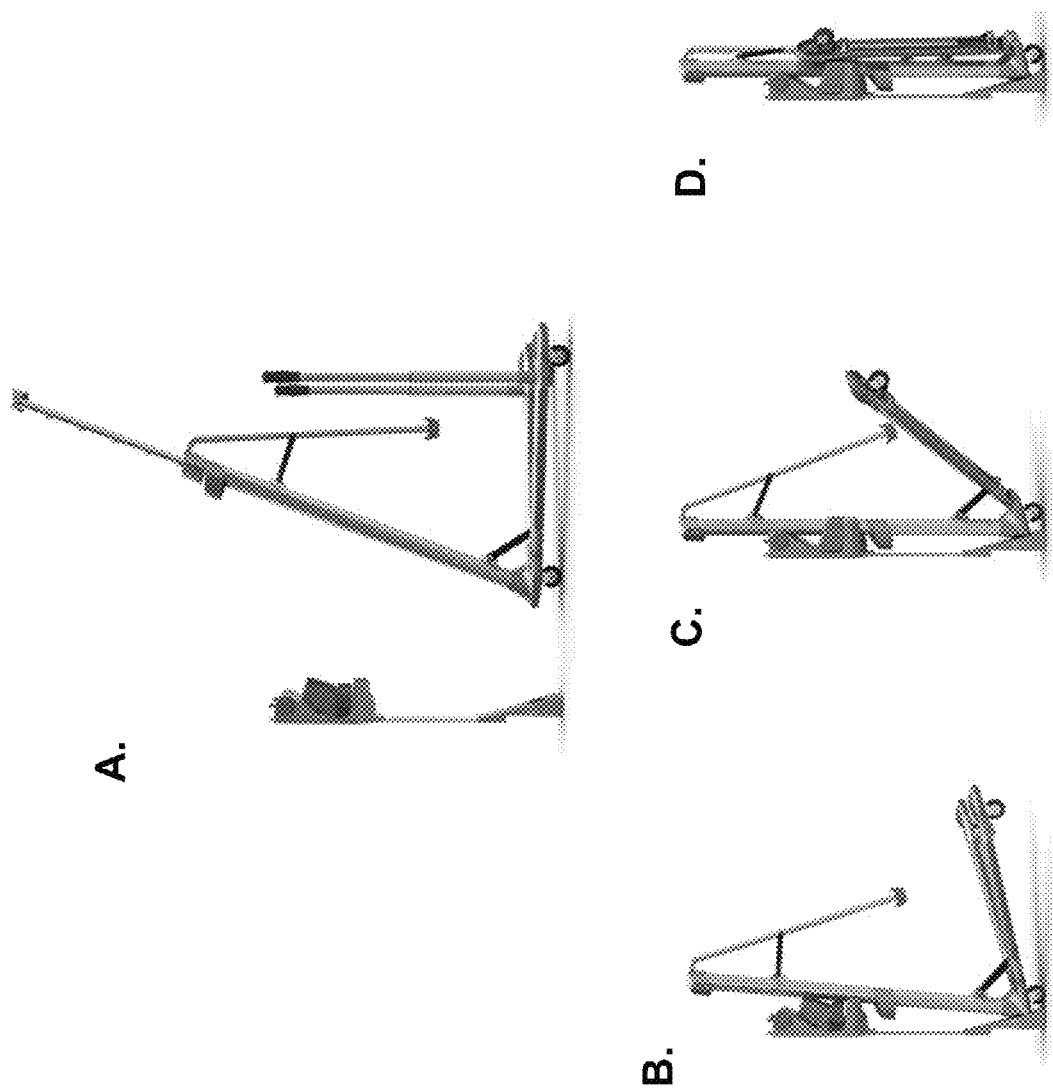
FIG. 18 illustrates a process for compactly storing and mounting an IMS to a wall. A. A deployed IMS is positioned in the vicinity to a wall-mounted holder (wall not shown). B. The apex region of the IMS is positioned in the apex catch of the holder and the arm holder and movable crown are stored; C. The trunk is secured by the head holder; D. The IMS is sully stored in a compact configuration adjacent to a wall surface and readily available for subsequent release and use.

FIGS. 6, 16 and 18 illustrate, in combination, an IMS and a holder apparatus with the IMS secured by the holder. In particular, the head holder portion securely holds the trunk, and specifically secures a trunk hold portion 780 that corresponds to a trunk location that is coincident with a portion of the longitudinal rails 830 of the movable crown system 800 when the crown system is in the stored configuration. In this example, the stored configuration corresponds to the top crown 810 nesting adjacent with the top 712 of the trunk 710, and the bottom crown 820 that is beneath both the holder catch mechanism 110 and the actuation slot 770.

Figure 13:
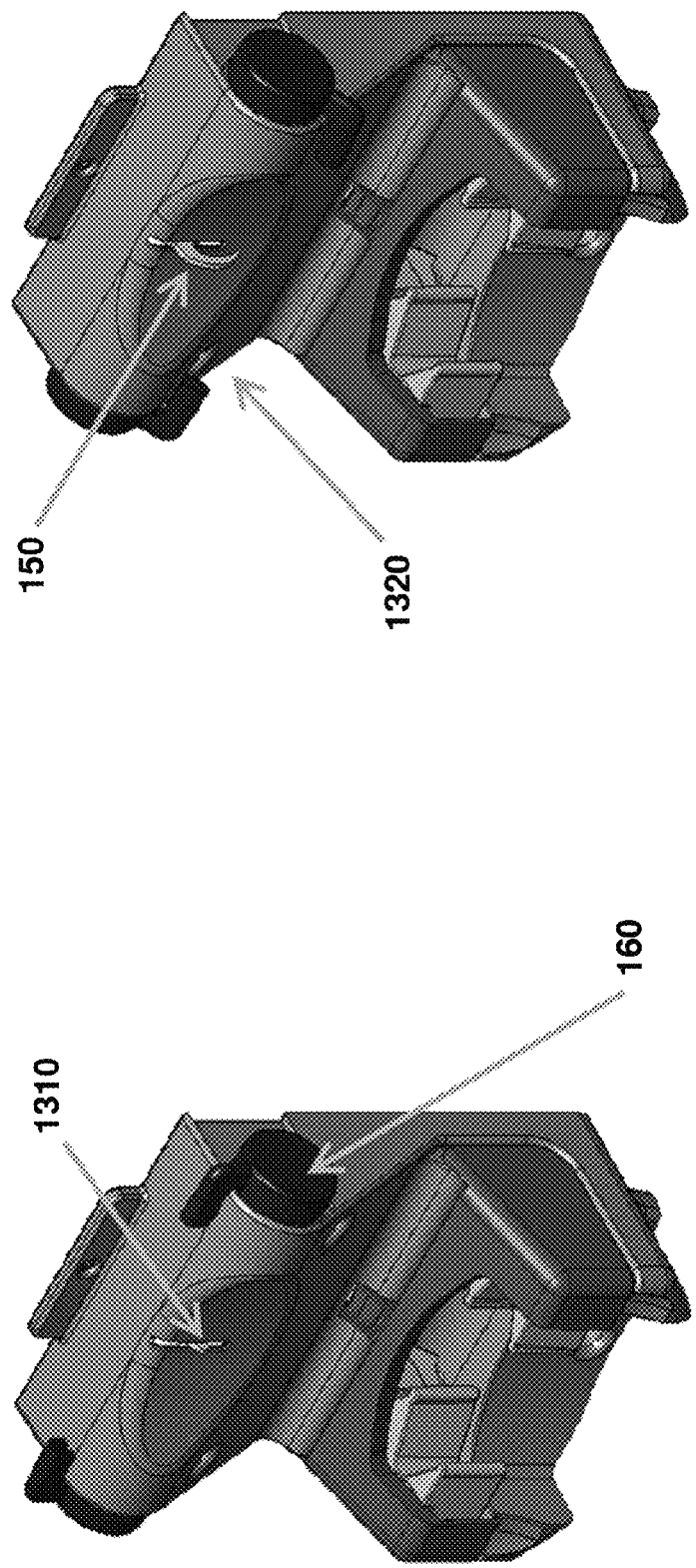
FIG. 13 is a schematic of a catch/release mechanism for aligning and further securing an IMS to the holder.
Figure 14:
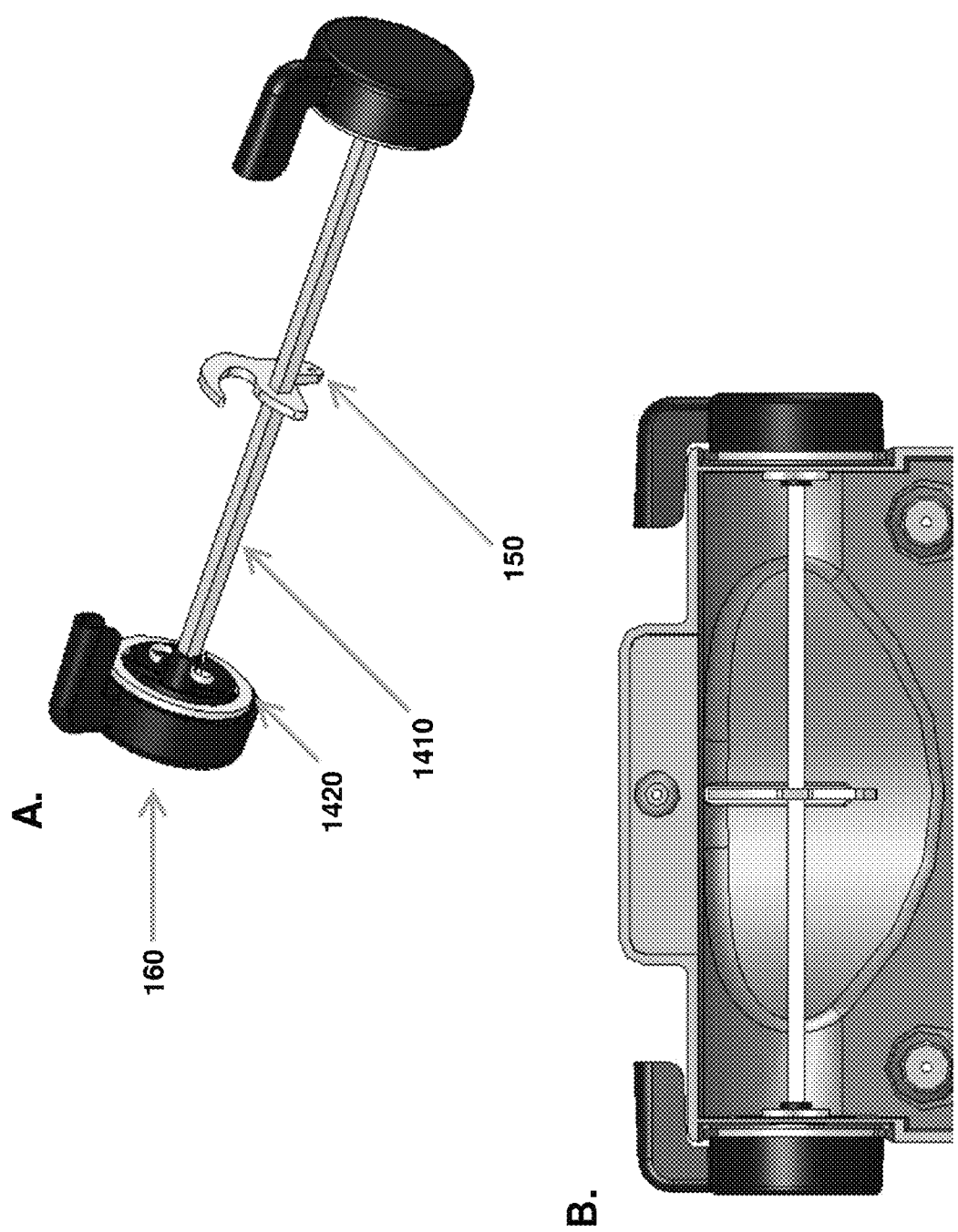
FIG. 14 is a schematic of a release handle that provides user-controllable reversible engagement of the release hook with a portion of the IMS trunk by incorporation of a shaft. A is a schematic of the rotatable connections. B illustrates the device of A incorporated into the housing head.

For further ease of use, especially for the common medical situation where only one caregiver either stores the IMS in the holder or must retrieve the IMS from the holder for patient use, an alignment holder may be incorporated into the holder. FIG. 14, focuses on this aspect of the holder, with the alignment holder corresponding to rotatable release handle 160 with a wear pad 1420 connected to a square shaft 1410 that is connected to release hook 150. In this manner, each of the elements is operably connected in that rotation of one component causes each of the other components to rotate. The bottom panel of FIG. 14 is a back view of the alignment holder incorporated into the head. FIG. 13 shows an alignment tab 1310, release hook 150, release handle 160 and a handle dead-stop 1320 in a closed (left panel) and released (right panel) configuration.

Figure 15:
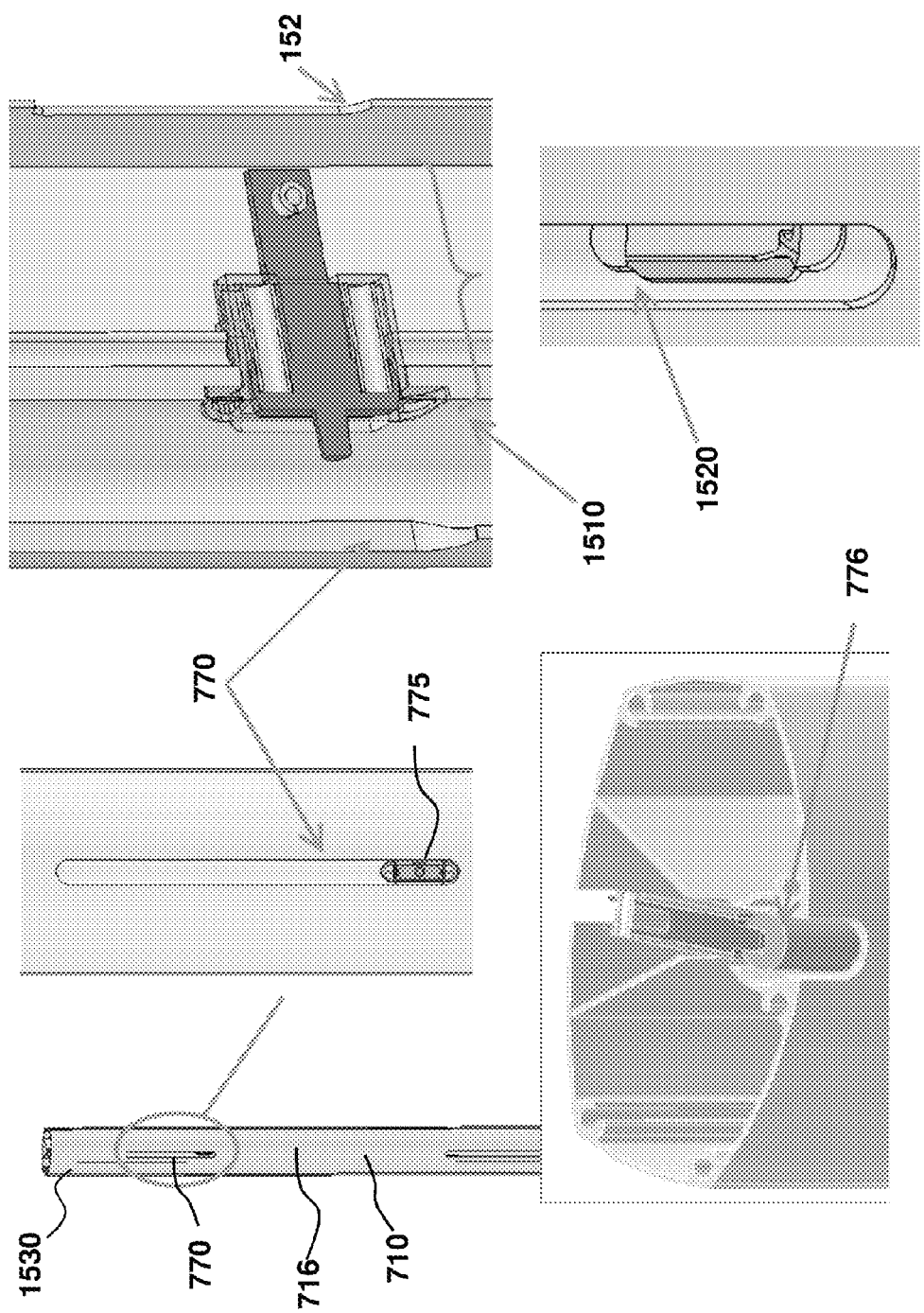
FIG. 15 is a schematic of the trunk portion of an IMS capable of reversibly engaging the release hook of the holder illustrated in FIGS. 13-14.

In an aspect, an actuation slot 770 is provided on a surface of the IMS trunk 710 for engaging the release hook 150, as summarized in FIG. 15. In an aspect, an actuation slot 770 is provided on the front surface 716 of the IMS trunk for engaging the release hook 150, as summarized in FIG. 15. The actuation slot 770 has a release mechanism 775 for facilitating rotation of IMS base arms relative to the trunk. In this manner, the IMS may be safely deployed and used without risk of unwanted rotation of base arms and subsequent instability or collapse of the IMS during use. In an aspect, the release mechanism 775 is connected to an actuation rod that, when engaged, allows the base arms to be rotated.

FIG. 16 illustrates a release hook also configured to provide alignment between the IMS and the holder. In particular, the release hook may comprise an alignment extension 154 that is positioned in actuation slot 770 to ensure the IMS is properly aligned with the holder head. Release handle 160 is rotated, thereby rotating the release hook 150 to engage the release mechanism 775 that is positioned in the actuation slot 770 of the IMS. In this example, the action of release hook 150 rotation while engaged with the release mechanism 775, physically pulls release mechanism 775 which, in turn, is connected to an actuation rod 776 (see FIG. 15) that when pulled by release mechanism allows base arms to rotate. In an aspect, the flappers close around the trunk and stored base arms, thereby securing the trunk and base arms to the holder head portion. Alternatively, the release hook 150 may be disengaged, thereby locking the base arms in the stored position, and the IMS trunk and base arms secured by the flappers that are in a closed configuration.

In an aspect, various tensioning means are incorporated into the device to at least partially automate the engage, release and rotation engagement. For example, release handle 160 is rotated to correspondingly move the hook 150. At sufficient rotation, the actuation rod 776 moves. Handle 160 may be spring-loaded, so that it returns to the original position. When the base arms are rotated into a stored position, such as parallel to the trunk, the base arms lock into position. This locking may be achieved by the shear pin assembly 1510 (shown in the main extrusion 1530 in FIG. 15) within a milled pocket 1520 engaging with a passage or hole in the actuation rod corresponding to a base arm-stored position. To release the base arms, handle 160 is again rotated and the base arms may rotate to a deployed position, the handle 160 is released and it returns to its original position by spring actuation. The shear pin then falls into another hole or passage in the actuation rod corresponding to a base arm-deployed configuration. In this configuration, the interaction of different passages or holes in the actuation rod and the shear pin along with spring loading, provides reliable base arm storage and deployment, facilitated by the release hook 150 of the IMS holder. In particular, the shear pin assembly and the release handle assemble are spring loaded, so that the shear pin assembly tends to push the pin into any available hole or passage and the handle and release hook tends to return to its original position.

A cut-away view of the IMS mounted to the holder is shown in the right panel of FIG. 16. In particular, the foot is specifically configured to receive the bottom portion of the trunk, and specifically a mountable protrusion 760 located on the leading edge of the apex region or nose cone of the IMS. The upper portion of the trunk (e.g., between the top crown and bottom crown), is reliable secured via the action of the flappers and locking head as well as the release hook.

FIGS. 17 and 18 provide a summary of IMS storage against a wall. FIG. 17 shows the apparatus 10 mounted to a wall surface and a deployed IMS 700. In FIG. 18A a fully-deployed IMS is brought into a position for mounting to a wall by the holder. The movable crown and handles are stored and the apex region is placed and secured in the foot apex catch (FIG. 18B). The trunk portion is rotated and engaged in the holder of the head (FIG. 18C). Base arms and pump mount are stored in a position that is substantially parallel to the trunk (FIG. 18D). The IMS is then ready for use by reversing the process summarized in FIG. 18. In this manner, a single person can easily store and mount the IMS and, similarly, deploy the IMS.

Unless explicitly otherwise defined herein, "substantially" refers to a value that deviates less than about 10% from the true value.

All references cited throughout this application, for example patent documents including issued or granted patents or equivalents; patent application publications; and non-patent literature documents or other source material are hereby incorporated by reference in their entireties, as though individually incorporated by reference, to the extent each reference is not inconsistent with the disclosure in this application (for example, a reference that is partially inconsistent is incorporated by reference except for the partially inconsistent portion of the reference).

This application relates to U.S. patent application Ser. Nos. 29/339,591 (80-09) filed Jul. 2, 2009, which is a continuation of 11/961,834 (173-06) filed Dec. 20, 2007, which claims benefit of 60/883,205 (173-06P) filed Jan. 3, 2007. This application further relates to U.S. patent application Ser. Nos. 29/355,328 (8-10) (now U.S. Pat. No. D630,731) and 29/355,329 (152-09) filed Feb. 5, 2010. Each of these patent applications are hereby incorporated by reference to the extent not inconsistent with the disclosure herein.

Every formulation or combination of components described or exemplified herein can be used to practice the invention, unless otherwise stated.

Whenever a range is given in the specification, for example, a size range or an angle range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein may be practiced in the absence of any element or elements, limitation or limitations which is not specifically disclosed herein.

One of ordinary skill in the art will appreciate that materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. An infusion management system and an apparatus for mounting the infusion management system to a wall, wherein the infusion management system comprises:
   a trunk having a bottom end and a top end that is at the opposite end of the trunk bottom end;
   an apex portion connected to the trunk bottom end;
   a first base arm connected to the trunk bottom end; and
   a second base arm connected to the trunk bottom end, wherein the first and second base arms define a two-sided base footprint;
and the apparatus comprises:
   a head comprising a holder for reversibly mounting at least a portion of the trunk of the infusion management system to the head; and
   a foot comprising an apex catch for reversibly mounting the apex portion of the infusion management system to the foot.

2. The infusion management system and apparatus of claim 1, wherein the holder comprises a pair of vertically opposed flappers that reversibly mounts the trunk of the infusion management system to the head.

3. The infusion management system and apparatus of claim 2, wherein the holder further comprises a locking hood operably connected to the flappers, wherein in a stored configuration the locking hood engages the flappers to secure the flappers in a closed position, and in an empty configuration the locking hood is not engaged to the flappers and the flappers are in an open configuration.

4. The infusion management system and apparatus of claim 3, the apparatus further comprising a flapper spring having a first end connected to a first flapper and a second end connected to a second flapper, wherein the flapper spring is in a stretched configuration when the locking hood is engaged with the pair of vertically opposed flappers and is in a relaxed configuration when the locking hood is not engaged with the pair of vertically opposed flappers.

5. The infusion management system and apparatus of claim 1, the apparatus further comprising an alignment holder, wherein the alignment holder comprises:
 a rotatable release hook connected to the head; and
 a rotatable release handle rotatably connected to the rotatable release hook,
 wherein rotation of the release handle rotates the rotatable release hook to align and secure the infusion management system to the head of the holder or to facilitate removal of the infusion management system from the head of the holder.

6. The infusion management system and apparatus of claim 5, the apparatus further comprising a shaft connected to the rotatable release hook and to the rotatable release handle.

7. The infusion management system and apparatus of claim 5, the apparatus further comprising:
 a guide face having a surface that substantially conforms to a trunk surface of the infusion management system; and
 a release hook slot positioned in the guide face, wherein the rotatable release hook at least partially extends through the release hook slot.

8. The infusion management system and apparatus of claim 7, wherein the guide face surface is at least partially concave to accommodate a convex shaped trunk surface.

9. The infusion management system and apparatus of claim 1, wherein the apex catch comprises:
 an opening; and
 an apex mount for securing the infusion management system apex region in the opening.

10. The infusion management system and apparatus of claim 1, wherein the foot comprises a tapered body, the tapered body having minimum taper at a top end and a maximum taper at a bottom end, wherein the apex catch is at least partially positioned in the bottom end.

11. The infusion management system and apparatus of claim 1, the apparatus further comprising a neck that connects to the head and the foot, wherein the neck has a first end connected to the head and a second end connected to the foot.

12. The infusion management system and apparatus claim 1, the apparatus further comprising fasteners for fastening the head, the foot, or both the head and the foot to a wall.

13. The infusion management system and apparatus of claim 1, the infusion management system further comprising a movable crown having a longitudinal rail that is substantially parallel to an outer surface of the trunk when the movable crown is in a stored configuration.

14. The apparatus of claim 13, the movable crown further comprising a top crown end at a top end of the longitudinal rail for supporting various medical-related items.

15. In combination, a holder apparatus and an infusion management system comprising:
 the holder apparatus comprising:
  a head comprising a holder; and
  a foot comprising an apex catch; and
 the infusion management system comprising:
  a trunk having a bottom end connected to an apex portion, and a top end
  a movable crown operably connected to the trunk, said movable crown having a bottom crown end, a top crown end and a longitudinal rail connecting the bottom crown end to the top crown end, wherein in a crown-stored configuration the movable crown spans a longitudinal crown portion of the trunk;
 wherein in combination with the holder apparatus and the infusion management system, the apex portion is positioned in the apex catch of the foot and a trunk hold portion positioned in the longitudinal crown portion of the trunk is secured by the holder.

16. A method of reversibly mounting an infusion management system to a receiving surface, said method comprising:
 providing an infusion management system comprising a trunk and an apex region;
 providing a surface mount comprising:
  a head connected to the surface, said head having a holder for receiving the infusion management system trunk; and
  a foot connected to the surface, said foot having an apex catch for receiving the apex region of infusion management system;
 positioning the apex region in the apex catch; and
 securing the head holder around the trunk, thereby reversibly mounting the infusion management system to the receiving surface.

17. The method of claim 16, wherein the receiving surface is a wall.

18. The method of claim 17, wherein the infusion management system further comprises a pair of base arms rotatably connected to the trunk, said method further comprising:
 rotating the pair of base arms to a position that is substantially parallel to the trunk so that the trunk and the base arms are in a stored configuration that is substantially parallel to the wall.

* * * * *